(12) United States Patent
Blömker et al.

(10) Patent No.: US 8,697,769 B2
(45) Date of Patent: Apr. 15, 2014

(54) LACQUER COMPOSITION COMPRISING A MONOMER WITH A POLYALICYCLIC STRUCTURE ELEMENT

(75) Inventors: Tobias Blömker, Cuxhaven (DE); Manfred Stepputtis, Kutenholz (DE); Reinhard Maletz, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 166 days.

(21) Appl. No.: 13/248,995

(22) Filed: Sep. 29, 2011

(65) Prior Publication Data

US 2012/0082637 A1  Apr. 5, 2012

(30) Foreign Application Priority Data

Sep. 30, 2010 (DE) .......................... 10 2010 041 789
Sep. 29, 2011 (EP) ..................................... 11183342

(51) Int. Cl.
*A61C 5/00* (2006.01)
*A61K 6/083* (2006.01)

(52) U.S. Cl.
USPC ........................................ 523/105; 424/78.31

(58) Field of Classification Search
USPC ............................ 106/36; 428/422.8; 523/115
See application file for complete search history.

(56) References Cited

U.S. PATENT DOCUMENTS

| | | |
|---|---|---|
| 3,681,296 A | 8/1972 | Hurwitz et al. |
| 4,160,080 A | 7/1979 | Koenig et al. |
| 4,323,348 A | 4/1982 | Schmitz-Josten et al. |
| 4,323,696 A | 4/1982 | Schmitz-Josten et al. |
| 4,420,306 A | 12/1983 | Orlowski et al. |
| 4,447,520 A | 5/1984 | Henne et al. |
| 4,744,828 A | 5/1988 | Winkel et al. |
| 4,772,530 A | 9/1988 | Gottschalk et al. |
| 4,874,450 A | 10/1989 | Gottschalk |
| 4,925,982 A | 5/1990 | Urano et al. |
| 4,954,414 A | 9/1990 | Adair et al. |
| 5,055,372 A | 10/1991 | Shanklin et al. |
| 5,057,393 A | 10/1991 | Shanklin et al. |
| 5,761,169 A | 6/1998 | Mine et al. |
| 6,020,528 A | 2/2000 | Leppard et al. |
| 6,617,413 B1 | 9/2003 | Bruchmann et al. |
| 6,632,481 B1 | 10/2003 | Blum et al. |
| 6,670,499 B1 | 12/2003 | Inoue et al. |
| 7,081,485 B2 | 7/2006 | Suh et al. |
| 7,148,382 B2 | 12/2006 | Wolf et al. |
| 7,264,882 B2 | 9/2007 | Engelbrecht |
| 7,381,785 B2 | 6/2008 | Detrembleur et al. |
| 7,872,058 B2 | 1/2011 | Uchida et al. |
| 8,013,032 B2 | 9/2011 | Uchida et al. |
| 2004/0034119 A1 | 2/2004 | Warford, II et al. |
| 2005/0288387 A1 | 12/2005 | Feng et al. |
| 2006/0063853 A1 | 3/2006 | Hurwitz et al. |
| 2006/0111465 A1 | 5/2006 | Jia et al. |
| 2007/0010597 A1 | 1/2007 | Klee et al. |
| 2007/0027229 A1 | 2/2007 | Moszner et al. |

FOREIGN PATENT DOCUMENTS

| | | |
|---|---|---|
| DE | 3338077 A1 | 5/1985 |
| DE | 3703120 A1 | 1/1988 |
| DE | 4231579 A1 | 3/1993 |
| DE | 4416857 C1 | 6/1995 |
| DE | 19903177 A1 | 7/2000 |
| DE | 10119831 A1 | 10/2002 |
| DE | 10352260 B3 | 4/2005 |
| DE | 102007040240 A1 | 2/2006 |
| DE | 60116142 T2 | 7/2006 |
| DE | 102006019092 A1 | 3/2007 |
| DE | 3941629 A2 | 10/2007 |
| DE | 102006050153 A1 | 5/2008 |
| DE | 102004060285 A1 | 6/2008 |
| DE | 102007048925 A1 | 4/2009 |
| DE | 102007040239 A1 | 5/2009 |
| DE | 102008039129 A1 | 5/2009 |
| DE | 102008010464 A1 | 8/2009 |
| EP | 0057474 A2 | 7/1979 |
| EP | 0007508 A2 | 2/1980 |
| EP | 0047902 A2 | 8/1981 |
| EP | 0049631 A1 | 10/1981 |
| EP | 0059451 A1 | 2/1982 |
| EP | 0106176 A1 | 4/1984 |
| EP | 0173567 A2 | 8/1985 |
| EP | 0184095 A2 | 11/1985 |
| EP | 0209700 A2 | 6/1986 |
| EP | 0262629 A2 | 9/1987 |
| EP | 0325266 A2 | 7/1989 |
| EP | 0366977 A2 | 10/1989 |
| EP | 0682012 A1 | 4/1995 |
| EP | 0712840 A1 | 5/1996 |
| EP | 0783880 A2 | 7/1997 |
| EP | 0948955 A1 | 6/1998 |
| EP | 0867457 A1 | 9/1998 |
| EP | 0980682 A1 | 6/1999 |
| EP | 1112995 B1 | 9/1999 |
| EP | 1236459 B1 | 7/2001 |
| EP | 1238993 A1 | 9/2002 |
| EP | 1532958 A1 | 5/2005 |
| EP | 1563821 A1 | 8/2005 |
| EP | 1545582 A1 | 4/2006 |
| EP | 1839640 A2 | 10/2007 |
| GB | 1110673 | 4/1968 |
| JP | 04029910 | 1/1992 |
| JP | 07206740 | 8/1995 |
| WO | 0130307 A1 | 5/2001 |
| WO | 0144873 A1 | 6/2001 |

(Continued)

*Primary Examiner* — Walter Webb
(74) *Attorney, Agent, or Firm* — Duane Morris LLP; J. Rodman Steele, Jr.; Gregory M. Lefkowitz

(57) ABSTRACT

A transparent lacquer composition that can be used as a protective and gloss lacquer for surface coating is described. The lacquer composition can be a dental material and a method for preparing a lacquer composition is also described. Also described are novel polymerizable monomers comprising at least one polyalicyclic structure element and certain ethylenic structure elements that are particularly suitable for use in a lacquer composition.

23 Claims, No Drawings

(56) References Cited

FOREIGN PATENT DOCUMENTS

| | | | |
|---|---|---|---|
| WO | 02092021 A1 | 11/2002 |
| WO | 02092023 A1 | 11/2002 |
| WO | 03035013 A1 | 5/2003 |
| WO | 2005084611 A1 | 9/2005 |
| WO | 2006063891 A1 | 6/2006 |
| WO | 2007028159 A2 | 3/2007 |
| WO | 2009065873 A2 | 5/2009 |

LACQUER COMPOSITION COMPRISING A MONOMER WITH A POLYALICYCLIC STRUCTURE ELEMENT

CROSS-REFERENCE TO RELATED APPLICATIONS

This application claims priority to German Patent Application No. DE 10 2010 041 789.0 filed Sep. 30, 2010, and European Patent Application No. EP 11 183 342 filed Sep. 29, 2011, the entireties of which are incorporated herein by reference.

FIELD OF THE INVENTION

The present invention relates to a, preferably transparent, lacquer composition, which can be used as a protective and gloss lacquer for surface coating. The invention also relates to a lacquer composition according to the invention as a dental material and a method for preparing a lacquer composition according to the invention. The invention further relates to novel polymerizable monomers comprising at least one polyalicyclic structure element and certain ethylenic structure elements, which are particularly suitable for use in a lacquer composition according to the invention, in particular a dental lacquer material according to the invention, and the use of the novel monomers in a lacquer composition.

BACKGROUND OF THE INVENTION

Temporary crowns and bridges in synthetic material are an important part of prosthetic treatment. An essential requirement of these materials is that they guarantee a smooth surface finish of the temporary prosthesis, since rough surfaces promote intra-oral plaque adhesion. If in the first place a bacterial film has formed, this can rapidly lead to inflammatory reactions of the periodontium and to gingivitis. A smooth surface also helps to prevent aesthetically problematical discolorations, such as for example those caused by coffee, tea, wine or cigarettes. The use of a tooth lacquer also provides a sheen to the surface of temporary prostheses with an otherwise matt appearance.

Generally surface smoothing of temporary prostheses is generally performed either with the help of polishes and polishing pastes or using unfilled or only very low-filled protective lacquer systems. Many investigations have shown that lacquered temporary prostheses demonstrate lower plaque build-up than polished surfaces. The reason for this is that when conventional polishing and abrasive bodies are used, all products to some extent leave behind working traces which are unavoidable when using mechanical polishing methods. For this reason the use of protective lacquers on these substrates is recommended.

When using a protective and gloss lacquer for coating of prostheses and temporary prostheses, account must be taken of the fact that the cured system after a certain dwell time on the prosthesis or the temporary prosthesis will have a rougher surface than directly after application of the lacquer. Such a situation can arise if the lacquer partly comes away from the synthetic material and leaves behind only "islands" with a gradual transition to residual synthetic material. At these points germ cells can then result in bacterial colonization.

Protective and gloss lacquers are known from the literature.

JP 4-29910 A describes the composition of a dental, colorless and transparent coating material that is claimed to have exceptional abrasion resistance. The lacquer contains a polyfunctional cross-linker, which is preparable through esterification of more than three hydroxyl groups of pentaerythritol or dipentaerthritol with acrylic acid (in particular pentaerythritol hexaacrylate), a volatile methacrylate compound (in particular methyl methacrylate) and an acyl phosphine oxide as the polymerization catalyst.

U.S. Pat. No. 7,081,485 B2 discloses a photocurable composition that can be used as a dental coating material, comprising a multiacrylate compound and a photoinitiator (acyl phosphine oxide), wherein the multiacrylate compound has at least five acrylate functionalities per molecule and the composition contains no methyl methacrylate and whereby the photoiniator is present in a quantity of less than 6 wt. % in the composition. The photoinitiator preferred here is 2,4,6-trimethylbenzoyl diphenyl phosphine oxide. The lacquer is claimed to cure free of any smear layers.

US 2005/0288387 A1 likewise relates to dental coating compositions that are claimed to cure without smear layers. These compositions are claimed to be storable with low odor and comprise a multiacrylate compound, a photoiniator (acyl phosphine oxide) and an alcohol, wherein ethanol is preferably used.

US 2004/0034119 A1 likewise discloses a dental material that is claimed to cure without a smear layer. Here a lacquer is initially applied to the tooth. In a second step a cover layer, for example a sealed, continuous layer of an essential oil, is applied to the surface of the lacquer. The lacquer is thus shielded from the surrounding atmosphere and can then be polymerized without a smear layer. The advantage of this method is claimed to be the fact that the covering layer, depending on the selection of its composition, provides an agreeable taste and or an agreeable smell during handling. Optionally the covering layer can be removed following polymerization.

US 2006/0111465 A1 claims dental polymerizable varnishes that contain a polymerizable, ethylenically unsaturated resin composition as well as a curing agent and a filler, which substantially constitutes a polyhedral oligomeric silsesquioxane.

EP 1 532 958 B1 is aimed at a dental coating material, that contains nanoscale particles with average particle sizes of 1 through 100 nm, that have been surface-modified, at least one polyfunctional methacrylate monomer, having four or a plurality of methacryloyl groups in a molecule and a photopolymerizator.

US 2007/0010597 A1 discloses laser-curable compositions for protecting the dental hard tissue. The compositions are single component and contain curable monomers with at least two polymerizable double bonds in the molecule and benzoyl peroxide as the initiator.

DE 10 2007 048 925 A1 describes coating and lacquering compositions which inter alia can be used for prostheses, lining materials or implants. The compositions described there are polysiloxane-based.

A further dental lacquer is disclosed in DE 10 2008 010 464 A1. In the event that, as detailed above, the lacquer layers over time, for example in abrasively stressed areas of the tooth surface, become permeable with the partial absence of lacquer and exposure of unprotected areas of the tooth surface, then a more intense build-up of bacterial deposits there is likely. For this reason tooth lacquers have been proposed that prevent or make more difficult the adherence of deposits to the lacquer. According to DE 10 2008 010 464 A1 this is claimed to be achieved by using a lacquer that through urethane groups in the dental material contains incorporated perfluorinated radicals. The perfluorinated alkyl groups that are incorporated into the lacquer formulation by reaction of perfluoro alcohols with isocyanate groups serve to render hydrophobic the surface of the cured system. Such hydrophobic surfaces are claimed to make more difficult or prevent the occurrence of deposits.

DE 10 2009 011 537 A1 relates to dental surface coating materials, which following polymerization lead to less discoloration. The lacquer system contains 2,4,6-trimethylbenzoyl diphenyl phosphine oxide as a photoinitiator and dimethacrylate bonds formed by ethylene oxide units, wherein the number of ethylene oxide structure elements is between 9 and 50. The lacquer can also contain a monomer such as dipentaerythrityl hexaacrylate.

DE 10 2009 011 536 A1 reports that the use of a (bis)acyl phosphine oxide compound such as 2,4,6-trimethylbenzoyl diphenyl phosphine oxide in combination with a diketone compound such as camphor quinine in the absence of an amine in a photocurable monomer system has a number of effects, e.g. an improvement in the curability in a broad wavelength range, reduction in the change in color tone before and after curing and an improvement in the thin layer surface curability. As preferred organic matrix monomers, dipentaerythrityl hexaacrylate and dimethacrylate compounds formed by alkylene oxide units are mentioned with the number of alykylene oxide structure elements being between 5 and 50.

DE 10 2008 039 129 A1 relates to transparent, scratch-proof coatings, which are also envisaged for use in dentistry. The coating material comprises a siloxane-containing matrix and functionalized single- and multiple-walled carbon nanotubes dispersed therein.

U.S. Pat. No. 6,617,413 B1 describes coating agents which can be hardened by the addition of isocyanate groups as well as by the radiation-induced addition of activated c-c double covalent bonds. The compounds described there can inter alia be used in dental compounds.

EP 1 307 173 B1 describes a fluoride lacquer and silicon-based fissure sealing material.

A temporary, transparent, dental lacquer composition for coating of tooth surfaces is described in US 2006/0063853 A1. Here the transparency is brought about by the addition of hollow glass balls, wherein the hollow glass balls divert any incoming light back to the light source. This effect is brought about by a total reflection that takes place inside the balls, which always occurs if light enters a hollow glass ball. This phenomenon is used in particular in road markings. In order to be able to create this effect, the refractive index of the binding agent must be less than that of the hollow glass balls.

As standard materials in the formulation of protective and gloss lacquers di(meth)acrylate-based synthetics are used with either no or only very little filling. Due to their lack of fillers or the only very low filler loading tooth lacquers, compared with flow and filling composites, tooth lacquers have even lower viscosities. They are as a rule thin- to medium-thin-flowing and are removed from a bottle with a microapplication instrument, for example with a small brush or small paintbrush and then applied directly. Alternatively the lacquer system can be applied from a syringe by means of needles.

Medium-thin-flowing or also slow-flowing materials can be better controlled during application while thin-flowing systems allow a thinner application and can also flow into very small cavities. The application in just a thin coating is therefore important so that occlusion with the antagonistic tooth is not lastingly disrupted. Furthermore, the thinner the application of the transparent lacquer, the more accurate is the impression given of the color of the lacquered tooth and thus the natural tooth situation.

However, as a result of the reduced amount of filler or the complete lack of this, the lacquer systems have lower resistance to abrasion and flexural strength than medium- to highly-filled materials.

If dental, radically curable compositions are polymerized, then the upper layer of the polymer often appears to be sticky. The surfaces have not totally cured. This phenomenon is triggered by the oxygen in the air, which is a triplet diradical, in that the oxygen molecules disrupt and inhibit the radical polymerization due to their radical nature. Such a moist-appearing layer must be removed with alcohol. If through the selection of the monomers and the selection and adjustment of the initiator system it is managed to prevent the formation of an oxygen inhibition layer, then this lacquer system will have better sheen characteristics and greater resistance to the influences of discoloring agents Low-filled or unfilled dental lacquering systems are suitable for use as "liquid polishing materials", "dental varnish", "coating materials", "protective lacquer", "gloss lacquer" and so on, for a large number of intra- and extra-oral situations and for use in the dental laboratory. Particularly suitable is their clinical use for coatings of the marginal areas of old and new, direct and indirect restorations in synthetic materials and synthetic material-reinforced glass ionomer cements, restorations and temporary prostheses for improving aesthetics and simplifying finishing and polishing, treatment of defects in the natural tooth structure.

The requirements on protective and gloss lacquer materials are therefore extremely varied. To begin with, transparent compositions should remain on the tooth surface for a long time in order to achieve their purpose. In so doing, they should withstand regular mechanical attacks on them for example from oral hygiene measures such as tooth brushing.

Since the lacquer materials in the oral cavity are exposed to permanent and highly-intensive hydrolytic attack, for example from saliva, the polymers should have the lowest possible water absorption. During radical cross-linking of methacrylate/acrylate compositions a three-dimensionally linked network results. Because of the very low size of the water molecule water can diffuse into the mesh of the polymer, where it accumulates at certain points in the network and there forms hydrogen bonds or other weak polar bonds. The more polar components that are present in the polymer matrix, the easier it is for further water absorption to take place. As a result of water absorption the polymer expands and an increase in the intermolecular distances take place. This hygroscopic expansion can lead to a structural reorganization of the polymer chains. The water absorption takes place over a long period following curing, so that when there is excessive water absorption an expansion stress occurs and thus an "overflowing" of the material. In the process parts of the lacquer may come away from the tooth surface and the above-mentioned "islands" form which then become the starting point for new bacterial colonizations.

On top of this water molecules can attack sensitive structure elements of the polymer such as for example ester groups, hydrolytically splitting these. This deterioration can lead to complete disintegration of the network and thus to a complete loss of the product.

On the other hand, a certain polarity of the lacquer systems is indeed desirable, since the tooth structure is hydrophilic and polar compositions guarantee a good adaptation and wettability of the material to the tooth substrate.

DESCRIPTION OF THE INVENTION

The primary object for the invention was to provide a lacquer composition, preferably a transparent lacquer composition, which is suitable for use as a protective and gloss lacquer, in particular in dentistry, and which has a low water consumption and very good mechanical characteristics. In addition, the lacquer composition should preferably be characterized by a very good adaptation, i.e. very good surface affinity to the corresponding surface, in particular the tooth structure. Furthermore the, preferably dental, lacquer composition should preferably cure without smear layers.

The primary object is achieved according to the invention by a, preferably transparent, lacquer composition, in particular a dental lacquer composition, consisting of or comprising (a) 35 through 99 wt. %, in relation to the total weight of the lacquer composition, of a monomer component comprising (a1)) one, two or a plurality of monomers selected from the group consisting of compounds (monomers) with the structure $Q(YZ_e)_b$, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups, b is an integer selected from the group of integers 1, 2, 3 and 4, each Z represents a structure element, which independently of any further structure elements Z is selected from the group consisting of
—O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$ and —O—CH=CH$_2$, each index e is an integer, which independently of any further indices e is selected from the group of integers 1, 2, 3 and 4, each Y represents a structure element, which in the structure $Q(YZ_e)_b$ bonds the polyalicyclic structure element Q with e structure elements Z, wherein each Y is selected independently of any further structure elements Y or is omitted, (a2) one, two or a plurality of radically polymerizable monomers selected from the group consisting of methyl methacrylate, ethyl methacrylate, propyl methacrylate, butyl methacrylate and pentyl methacrylate, (a3) optionally one, two or a plurality of further radically polymerizable monomers selected from the group consisting of monomers with three or a plurality of (meth)acrylate groups, preferably with three to six (meth)acrylate groups, and (a4) optionally one, two or a plurality of further radically polymerizable monomers from the group consisting of acrylates and methacrylates, preferably from the group of methacrylates, and (b) one or a plurality of initiators and/or catalysts, and (c) optionally a filler component comprising one, two or a plurality of fillers, (d) optionally one or a plurality of further additives.

In other words the present invention relates to a preferably transparent lacquer composition, in particular a dental lacquer composition, consisting of or comprising (a) 35 through 99 wt. %, in relation to the total weight of the lacquer composition, of a monomer component comprising (a1)) one, two or a plurality of monomers selected from the group consisting of compounds (monomers) with the structure $Q(Y_xZ_e)_b$, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups (here preferably C1-C4-alkyl), alkoxy groups (here preferably C1-C4-alkoxy), halogen atoms (here preferably F) or trifluormethyl groups, b is an integer selected from the group of integers 1, 2, 3 and 4, each Z represents a structure element, which independently of any further structure elements Z is selected from the group consisting of
—O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$ and —O—CH=CH$_2$, each index e is an integer, which independently of any further indices e is selected from the group of integers 1, 2, 3 and 4, each index x independently of any further indices x represents 0 or 1, each Y in the structure $Q(Y_xZ_e)_b$ where x=1 represents a structure element, which bonds the polyalicyclic structure element Q with e structure elements Z, wherein each Y is selected independently of any further structure (a2) one, two or a plurality of radically polymerizable monomers selected from the group consisting of methyl methacrylate, ethyl methacrylate, propyl methacrylate, butyl methacrylate and pentyl methacrylate, (a3) optionally one, two or a plurality of further radically polymerizable monomers selected from the group consisting of monomers with three or a plurality of (meth)acrylate groups, preferably with three to six (meth)acrylate groups, wherein the further radically polymerizable monomers of component (a3) are not monomers according to the definitions under (a1) or (a2), and (a4) optionally one, two or a plurality of further radically polymerizable monomers from the group consisting of acrylates and methacrylates, preferably from the group of methacrylates, wherein the further radically polymerizable monomers of component (a4) are not monomers according to the definitions under (a1), (a2) or (a3), and (b) one or a plurality of initiators and/or catalysts and (c) optionally a filler component comprising one, two or a plurality of fillers, (d) optionally one or a plurality of further additives.

Within the context of the present text (meth)acrylic means both acrylic and methacrylic.

All the statements below relating to the compounds of structure $Q(YZ_e)_b$ (wherein each Y is selected independently of any further structure elements Y or is omitted) and the preferred or particularly preferred configurations of the present invention indicated in connection with these compounds apply accordingly to the compounds of structure $Q(Y_xZ_e)_b$ (wherein each index x independently of any further indices x represents 0 and 1), and vice versa.

A compound according to the invention or to be used according to the invention of structure $Q(Y_xZ_e)_b$ comprises a polyalicyclic structure element Q, which is derived from a corresponding polyalicyclic hydrocarbon. In the context of the present text, this means that b hydrogen atoms of the hydrocarbon are replaced by substituents $Y_xZ_e$ (as described above), and optionally one, two or a plurality of the hydrogen atoms not substituted by $Y_xZ_e$ are substituted by alkyl groups, alkoxy groups, halogen atoms or trifluoromethyl groups. The polyalicyclic structure element Q is constituted by carbon ring atoms. Carbon atoms outside the rings are a constituents of substituents.

Naturally, for substances which because of their structure at the same time fall under the definition of various component of a lacquer composition according to the invention it is the case that for quantitative considerations these substances must be assigned in each case to all these components.

The "polyalicyclic" structure element Q is a bicyclic, tricyclic, tetracyclic, pentacyclic or hexacyclic hydrocarbon radical as defined above. The designations "bicyclic", "tricyclic", "tetracyclic", "pentacyclic" and "hexacyclic" here correspond to the IUPAC nomenclature.

Preferably each Y represents a structure element, which in the structure $Q(Y_xZ_e)_b$ with x=1, bonds the polyalicyclic structure element Q with e structure elements Z, wherein each Y is selected independently of any further structure elements Y.

It has been found that the lacquer compositions according to the invention are dental protective and gloss lacquers which, compared to lacquers from the state of the art, demonstrate a much better surface affinity (in particular to the dry tooth enamel), absorb very much less water and have good mechanical properties (in particular flexural strength and modulus of elasticity).

The lacquer composition according to the invention is preferably photocurable.

The total of the numerical values of the index b and the index e is preferably 3, 4, 5, 6, 7 or 8.

Our own research has surprisingly shown that a lacquer composition according to the invention, in particular a lacquer composition according to the invention, which comprises one, two or a plurality of monomers of structure $Q(YZ_e)_b$ (as defined above and wherein each Y is selected independently of any further structure elements Y or is omitted) of component (a1),
and
(a2) one, two or a plurality of further radically polymerizable monomers selected from the group consisting of methyl methacrylate, ethyl methacrylate, propyl methacrylate, butyl methacrylate and pentyl methacrylate, preferably methyl methacrylate, and preferably in addition (a3) one, two or a plurality of further radically polymerizable monomers with three or a plurality of (meth)acrylate groups, preferably with three to six (meth)acrylate groups, in the cured state has low shrinkage, good adhesion to various substrates, high resistance to hydrolysis, low water absorption, high mechanical strength and high sheen The stated characteristics are important in particular in the area of dental engineering.

Preference is for a lacquer composition according to the invention, in which the monomer component (a) comprises or consists of (a1) one, two or a plurality of monomers of structure $Q(YZ_e)_b$ (as defined above and wherein each Y is selected independently of any further structure elements Y or is omitted) of component (a1), wherein Z preferably represents a —O—(C=O)—CH=CH$_2$, —O—(C=O)—C(CH$_3$)=CH$_2$, —(C=O)—CH=CH$_2$ or —(C=O)—C(CH$_3$)=CH$_2$ group, (a2) one, two or a plurality of radically polymerizable monomers selected from the group consisting of methyl methacrylate, ethyl methacrylate, propyl methacrylate, butyl methacrylate and pentyl methacrylate, (a3) one, two or a plurality of further radically polymerizable monomers with three or a plurality of (meth)acrylate groups, preferably with three to six (meth)acrylate groups, and (a4) optionally one, two or a plurality of further radically polymerizable monomers from the group consisting of acrylates and methacrylates, preferably from the group of methacrylates.

According to the invention preference is for a lacquer composition in which the monomer component (a) comprises or consists of (a1) one, two or a plurality of monomers of structure $Q(Y_xZ_e)_b$ of component (a1), wherein Z preferably represents a —O—(C=O)—CH=CH$_2$, —O—(C=O)—C(CH$_3$)=CH$_2$, —(C=O)—CH=CH$_2$ or —(C=O)—C(CH$_3$)=CH$_2$ group, (a2) one, two or a plurality of radically polymerizable monomers from the group consisting of methyl methacrylate, ethyl methacrylate, propyl methacrylate, butyl methacrylate and pentyl methacrylate, (a3) one, two or a plurality of further radically polymerizable monomers with three or a plurality of (meth)acrylate groups, preferably with three to six (meth)acrylate groups, wherein the further radically polymerizable monomers of component (a3) are not monomers according to the definitions under (a1) or (a2),
and (a4) optionally one, two or a plurality of further radically polymerizable monomers from the group consisting of acrylates and methacrylates, preferably from the group of methacrylates, wherein the further radically polymerizable monomers of component (a4) are not monomers according to the definitions under (a1), (a2) or (a3).

Preference is for a lacquer composition according to the invention comprising or consisting of:

(a) 38 through 96 wt. % of a monomer component comprising
(a1) one, two or a plurality of monomers of structure $Q(YZ_e)_b$ (as defined above and wherein each Y is selected independently of any further structure elements Y or is omitted) of component (a1), wherein Z preferably represents a —O—(C=O)—CH=CH$_2$, —O—(C=O)—C(CH$_3$)=CH$_2$, —(C=O)—CH=CH$_2$ or —(C=O)—C(CH$_3$)=CH$_2$ group, (a2) one, two or a plurality of radically polymerizable monomers selected from the group consisting of methyl methacrylate, ethyl methacrylate, propyl methacrylate, butyl methacrylate and pentyl methacrylate, (a3) one, two or a plurality of further radically polymerizable monomers with three or a plurality of (meth)acrylate groups, preferably with three to six (meth)acrylate groups,
and (a4) optionally one, two or a plurality of further radically polymerizable monomers from the group consisting of acrylates and methacrylates, preferably from the group of methacrylates, wherein the ratio of the weight of component (a1) to the total weight of component (a2), (a3), and (a4) is preferably in the range 4:1 through 1:6,
(b) one or a plurality of initiators and/or catalysts,
(c) 0 through 60 wt. % of a filler component, comprising one, two or a plurality of fillers selected from the group consisting of
  (c1) 0 through 60 wt. % of non-agglomerated, preferably surface-modified nanoparticles with an average particle size of less than 200 nm (preferably less than 100 nm, particularly preferably less than 60 nm),
  (c2) 0 through 10 wt. % of microparticles with an average particle size of 0.4 µm through 10 µm, and
  (c3) 0 through 15 wt. % of further fillers, preferably 0 through 10 wt. %, preferably 0 through 5 wt. %, more preferably 0 through 2.5 wt. % of further fillers,
and
(d) optionally one or a plurality of additives,
wherein the weight percentages given in each case relate to the total weight of the lacquer composition.

Preferably the total quantity of component (a1) and component (a2) in a lacquer composition according to the invention is at least 25 wt. %, preferably 30 wt. % or more, preferably 35 wt. % or more, in each case in relation to the total weight of the lacquer composition.

Preferably the total quantity of components (a1), (a2) and (a3) in a lacquer composition according to the invention is at least 38 wt. %, preferably 40 wt. % or more.

In preferred configurations the total amount of components (a1), (a2) and (a3) in a lacquer composition according to the invention is in the range 40 through 96 wt. %, more preferably in the range 50 through 95 wt. %, more preferably in the range 60 through 95 wt. %, more preferably in the range 70 through 95 wt. %, in each case in relation to the total weight of the lacquer composition.

In the uncured state a lacquer composition according to the invention, in particular a dental lacquer composition according to the invention, is characterized by a low contact angle to the dry tooth enamel (preferably of less than 50°, preferably less than 40°, particularly preferably less than 30°, measured with a contact angle measuring instrument from Krüss (DSA 100)). Before performing the contact angle measurement to this end a human tooth was dried with a tissue ("dry tooth enamel").

It has further become apparent that a lacquer composition according to the invention, in particular a dental lacquer composition according to the invention, in the cured state has a very low water absorption, and preferably less than 50 µg/mm$^3$, preferably less than 45 µg/mm$^3$, and preferably less than 40 µg/mm$^3$, particularly preferably less than 35 µg/mm$^3$. Here the water absorption was determined analogous to ISO 4049.

The lacquer compositions according to the invention have a variety of uses on different substrates and are preferably used as cavity and surface lacquer in dentistry. The lacquer compositions according to the invention are preferably used on glass ionomer fillings, temporary crowns and bridges in composite and on composite restorations. The adhesive "interfaces" between composite and tooth structure can be protected by lacquer compositions according to the invention.

As cavity lacquers the lacquer compositions according to the invention can be used for underfilling tooth filling materials and in so doing shield the pulp from damaging monomers. As a surface lacquer the lacquer compositions according to the invention can protect the tooth enamel from external negative impacts and from the substances present in the oral cavity and on the tooth surface preventing the occurrence of caries.

When used on composite surfaces in definitive composite restorations, a lacquer composition according to the invention serves to prevent premature attrition of the restoration. As a result it improves the wear resistance of the underlying filling material. A lacquer composition according to the invention brings about lasting stability of the restored surfaces and protects against abrasion and discoloration. Because of their extremely low viscosities lacquer compositions according to the invention are able to flow into marginal gaps, fill and thus close these. The same behavior is demonstrated by them for microcracks on restorative surfaces.

On top of this, the lacquer compositions according to the invention meet demanding aesthetic requirements. Through the application of a very thin layer of a lacquer composition according to the invention, a long-lasting, high-gloss, extremely smooth surface forms. A lacquer composition according to the invention thus gives the tooth or the restoration a natural gloss through the formation of aesthetic surfaces. As a result of the fine surface smoothness the risk of deposits of coloring matter is reduced.

The lacquer compositions according to the invention can also be used for surface enhancement of temporary crowns and bridges.

Dental lacquer compositions according to the invention are preferably designed so that they can be used as cavity and/or surface lacquer, as an underfilling for dental filling materials, to protect the tooth enamel, to prevent caries, to protect a restoration (in particular from premature attrition), to improve the resistance to abrasion of a dental filling material, to stabilize restored surfaces, to protect against abrasion and/or discoloration of a tooth or a restoration, to close marginal gaps and/or microcracks, to smooth restored surfaces, to provide a natural sheen to a tooth or restoration and to reduce deposits of coloring matter on a tooth or a restoration. Corresponding uses of a lacquer composition according to the invention are preferred.

Constituent (a): Monomer Component

In a lacquer composition according to the invention the function of the monomer component (a) is to form a matrix. This matrix is formed by polymerization, in particular radical polymerization of one, two or a plurality of monomers of structure $Q(YZ_e)_b$ (as defined above and wherein each Y is selected independently of any further structure elements Y or is omitted) of component (a1)) together with one or a plurality of further monomers of components (a2), (a3) and (a4). The monomer component (a) is a monomer mixture, which comprises or consists of component (a1)) and component (a2) and optionally component (a3) and optionally component (a4).

Here the ratio of the weight of component (a1) to the total weight of components (a2), (a3), and (a4) is preferably in the range 4:1 through 1:6, preferably in the range 3:1 through 1:3.

The total quantity of component (a1)) is preferably at least 10 wt. %, preferably at least 15 wt. %, in reach case in relation to the total weight of the lacquer composition according to the invention.

The total quantity of component (a1) is preferably in the range 10 through 80 wt. %, preferably in the range 15 through 75 wt. %, in each case in relation to the total weight of the lacquer composition according to the invention.

The polyalicyclic structure element Q of component (a1) here ensures a sterically rigid and hydrophobic spine, the methacrylate monomers of components (a2) ensure rapid polymerization kinetics and the optional monomers of components (a3) and/or (a4) ensure sufficient cross-linking. The latter applies in particular also in relation to the surface-modified fillers, where present.

Particularly preferred lacquer compositions according to the invention contain both component (a2) and component (a3).

A combination of component (a2) and component (a3) allows fine adjustment of the mechanical and rheological characteristics of a lacquer composition according to the invention. In particular through a combination of highly functionalized acrylate compounds of component (a3) with the extremely mobile monofunctionalized monomers of low molecular weight of component (a2), as a result of diffusion processes rapid polymerization kinetics are generated and thus a rapidly-curing lacquer composition is created.

Component (a1): One, Two or a Plurality of Monomers of Structure $Q(YZ_e)_b$ with at Least One Polyalicyclic Structure Element Component (a1) is comprised one, two or a plurality of monomers of the structure $Q(YZ_e)_b$ defined above (as defined above and wherein each Y is selected independently of any further structure elements Y or is omitted) wherein Z preferably represents a structure element selected independently of any further structure elements Z from the group consisting of —O—(C=O)—CH=CH$_2$, —O—(C=O)—C(CH$_3$)=CH$_2$, —(C=O)—CH=CH$_2$ or —(C=O)—C(CH$_3$)=CH$_2$. Preference is for compounds of structure $Q(YZ_e)_b$ (as defined above and wherein each Y is selected independently of any further structure elements Y or is omitted), wherein Z is selected from the group consisting of —O—(C=O)—CH=CH$_2$, —O—(C=O)—C(CH$_3$)=CH$_2$, that is to say those compounds of structure $Q(YZ_e)_b$ (as defined above and wherein each Y is selected independently of any further structure elements Y or is omitted) which have one, two or a plurality of acrylate and/or methacrylate groups, preferably two or a plurality of acrylate and/or methacrylate groups.

The polymers and products obtainable with the monomers of component (a1) according to the invention or to be used according to the invention have a pronounced hydrophobia which inter alia manifests itself in very low water absorption of the polymers and products. Additionally, the polymers obtainable by using the monomers of component (a1) according to the invention or to be used according to the invention are characterized by high mechanical stability which inter alia manifests itself in a high flexural strength of the polymers. The monomers of component (a1)) in particular according to the invention or to be used according to the invention, according to the particularly preferred configurations and embodiments, lend themselves to processing into polymers which in the cured state have both a low water absorption and a high flexural strength.

It has further been found that the monomers of component (a1) according to the invention or to be used according to the invention have usable, comparatively low viscosities. These monomers of component (a1) are copolymerizable with the further monomers of component (a2) and optionally of component (a3) and optionally of component (a4), wherein the cured polymers or molding materials have low shrinkage, good adhesion to various substrates, high resistance to hydrolysis, low water absorption, suitable mechanical strength and a high sheen. The stated characteristics are important in particular in the area of dental engineering.

The preferred and particularly preferred compounds of component (a1) according to the invention or to be used according to the invention, in particular, allow a high degree of cross-linking and are also preferably radically cross-linkable. Due to their highly functionalized structure they have a high probability of cross-linking and polymerization.

Preferred compounds according to the invention or to be used according to the invention are those wherein Q represents a polyalicyclic structure element, preferably a saturated polyalicyclic structure element, selected from the group consisting of bicyclic and tricyclic hydrocarbon radicals, wherein preferably none of the hydrogen atoms of this polyalicyclic structure element Q not substituted by substituents $YZ_e$ (as defined above and wherein each Y is selected independently of any further structure elements Y or is omitted) is substituted.

Insofar as a compound according to the invention comprises two or a plurality of polyalicyclic structure elements, these may be identical or different.

Particularly preferred are monomers $Q(YZ_e)_b$ according to the invention or to be used according to the invention (as defined above and wherein each Y is selected independently of any further structure elements Y or is omitted), the polyalicyclic structure element Q of which is derived from the following tricyclic hydrocarbons: tricyclo[5.2.1.0$^{2,6}$]decane (TCD), tricyclo[5.2.1.0$^{2,6}$]dec-3-ene or tricyclo[3.3.1.1$^{3,7}$]decane (adamantane), i.e. preference is for compounds according to the invention, which have a TCD structure, a tricyclo[5.2.1.0$^{2,6}$]dec-3-ene structure or an adamantane structure.

Tthe stated particularly preferred compounds according to the invention or to be used according to the invention, in which the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical, are preferably those with a tricyclo[5.2.1.0$^{2,6}$]decane structure, a tricyclo[5.2.1.0$^{2,6}$]dec-3-ene structure, a tricyclo[3.3.1.1$^{3,7}$]decane structure or a bicyclo[2.2.1]heptane structure, in which in each case none of the hydrogen atoms of this polyalicyclic structure element Q not substituted by substituents $YZ_e$ (as defined above and wherein each Y is selected independently of any further structure elements Y or is omitted) is substituted.

Particularly preferred compounds according to the invention or to be used according to the invention are those wherein the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical, and particularly preferred the structure element Q represents a tricyclo[5.2.1.0$^{2,6}$]decane radical or a tricyclo[5.2.1.0$^{2,6}$]dec-3-ene radical.

Preference is for the use of methacrylic acid or acrylic acid esters with a tricyclo[5.2.1.0$^{2,6}$]-decane or tricyclo[5.2.1.0$^{2,6}$]-decene structure element, selected from the group consisting of 8,9-bis(acryloxymethyl)tricyclo[5.2.1.0$^{2,6}$]decane
  8,9-bis(methacryloyloxymethyl)tricyclo[5.2.1.0$^{2,6}$]decane
  8,9-[bis(2-vinyloxyethyl)oxymethyl]tricyclo[5.2.1.0$^{2,6}$]dec-3-ene
  8,9-[bis(2-vinyloxyethyl)oxymethyl]tricyclo[5.2.1.0$^{2,6}$]decane
  8-hydroxymethyl-9-(2-vinyloxyethyl)oxymethyl]tricyclo[5.2.1.0$^{2,6}$]dec-3-ene
  9-hydroxymethyl-8-(2-vinyloxyethyl)oxymethyl]tricyclo[5.2.1.0$^{2,6}$]dec-3-ene
  8,9-bis(acryloyloxymethyl)tricyclo[5.2.1.0$^{2,6}$]dec-3-ene
  8,9-bis(methacryloyloxymethyl)tricyclo[5.2.1.0$^{2,6}$]dec-3-ene
  diacrylic acid esters or dimethacrylic acid esters of compounds selected from the group consisting of:
  3,8-dihydroxymethyl-tricyclo[5.2.1.0$^{2,6}$]decane
  3,9-dihydroxymethyltricyclo-[5.2.1.0$^{2,6}$]decane 4,8-dihydroxymethyltricyclo[5.2.1.0$^{2,6}$]decane
3,8-dihydroxytricyclo[5.2.1.0$^{2,6}$]decane
3,9-dihydroxytricyclo-[5.2.1.0$^{2,6}$]decane
4,8-dihydroxytricyclo[5.2.1.0$^{2,6}$]decane
methacrylic acid or acrylic acid esters of compounds from the group consisting of:
poly(hydroxymethyl)tricyclo[5.2.1.0$^{2,6}$]decanyl-siloxanes
oxyalkylated bishydroxymethyltricyclo[5.2.1.0$^{2,6}$]decane
oxyalkylated bishydroxytricyclo[5.2.1.0$^{2,6}$]decane
urethane- or urea groups-containing methacrylic acid or acrylic acid esters of compounds selected from the group consisting of:
3,8-dihydroxymethyl-tricyclo[5.2.1.0$^{2,6}$]decane
4,8-dihydroxymethyl-tricyclo[5.2.1.0$^{2,6}$]decane
3,9-dihydroxymethyl-tricyclo[5.2.1.0$^{2,6}$]decane
4,9-dihydroxymethyl-tricyclo[5.2.1.0$^{2,6}$]decane Here in the stated compounds hydrogen in the tricyclo[5.2.1.0$^{2,6}$]-decane- or tricyclo[5.2.1.0$^{2,6}$]-decene radical can be substituted by alkyl groups (here preferably C1-C4-alkyl), alkoxy groups (here preferably C1-C4-alkoxy), halogen atoms (here preferably F) or trifluoromethyl groups.

Many of the radically polymerizable methacrylic acid or acrylic acid esters listed above with a TCD structure element are known from the prior art.

Our own research has also shown that in particular with the monomers $Q(YZ_e)_b$ (as defined above and wherein each Y is selected independently of any further structure elements Y or is omitted) of component (a1) with a tricyclo[5.2.1.0$^{2,6}$]-decane structure element of component (a1) mentioned above or below lacquer compositions with a low contact angle to the dry tooth enamel (preferably less than 40°, preferably less than 30°) and low water absorption (preferably less than 40 µg/mm$^3$, preferably less than 35 µg/mm$^3$) can be obtained.

Y is preferably a structure element that in the structure $Q(Y_xZ_e)_b$ links the polyalicyclic structure element Q with e structure elements Z and contains or comprises a structure element that is selected from the group consisting of

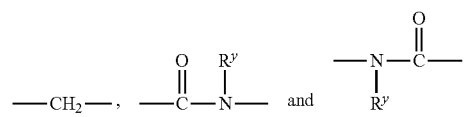

wherein $R^y$ represents another radical of the compound and wherein in each case the bond arranged to the left of the graphic formula is closer to the structure element Q and the bond arranged on the right is closer to the structure element Z.

The other radical $R^y$ of a compound according to the invention or to be used according to the invention is preferably selected from the group consisting of hydrogen, linear, branched or ring-comprising structure elements with 1 through 50 C atoms and 0 through 12 heteroatoms, wherein the heteroatoms that are optionally present are preferably selected from the group consisting of N and O.

The other radical $R^y$ here is preferably selected from the group consisting of hydrogen, linear, branched or ring-comprising structure elements with 1 through 40 C atoms and 0 through 10 heteroatoms, wherein the heteroatoms that are optionally present are preferably selected from the group consisting of N and O.

The other radical $R^y$ here is particularly preferably selected from the group consisting of hydrogen, linear, branched or ring-comprising structure elements with 1 through 35 C atoms and 1 through 10 heteroatoms, wherein the heteroatoms that are optionally present are preferably selected from the group consisting of N and O.

Here Y is preferably a structure element containing or consisting of a structure element selected from the group consisting of

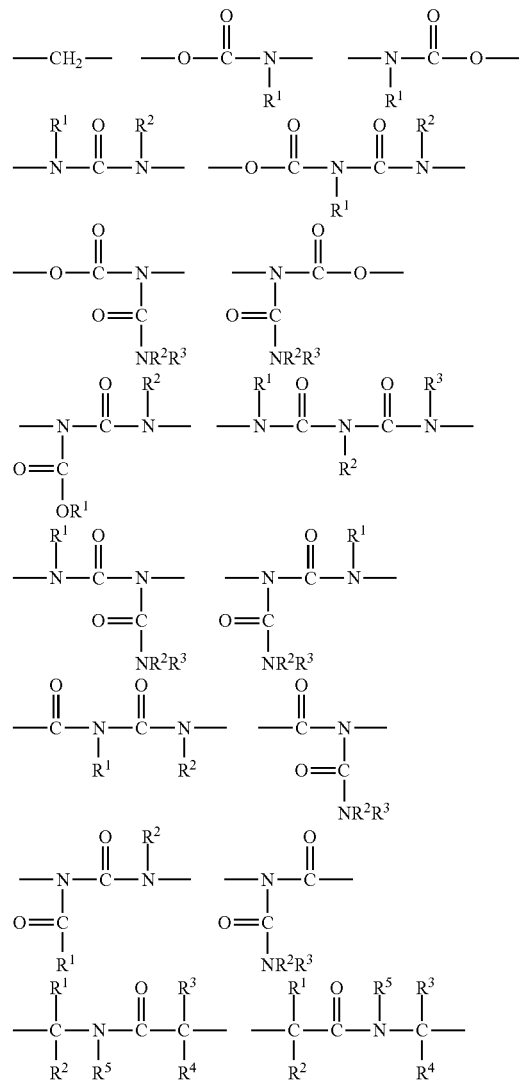

wherein $R^1$, $R^2$, $R^3$ R4 and $R^5$ represent other radicals of the compound, wherein in each case the bond arranged to the left of the graphic formula is closer to the structure element Q and the bond arranged on the right is closer to the structure element Z.

The above-mentioned radicals $R^1$, $R^2$ R3, $R^4$ or $R^5$ of a compound according to the invention or a compound to be used according to the invention of structure $Q(Y_xZ_e)_b$ are, in each case independently of one another, preferably selected from the group consisting of hydrogen, linear, branched or ring-comprising structure elements with 1 through 30 C atoms and 0 through 10 heteroatoms, wherein the heteratoms that are optionally present are preferably selected from the group consisting of N and O.

Here the other radicals $R^1$, $R^2$, $R^3$, $R^4$ or $R^5$, in each case independently of one another, are preferably selected from the group consisting of hydrogen, linear, branched or ring-comprising structure elements with 1 through 25 C atoms and 0 through 8 heteroatoms, wherein the heteroatoms that are optionally present are preferably selected from the group consisting of N and O.

Here the other radicals $R^1$, $R^2$, $R^3$, $R^4$ or $R^5$, in each case independently of one another, are particularly preferably selected from the group consisting of hydrogen, linear, branched or ring-comprising structure elements with 1 through 20 C atoms and 0 through 5 heteroatoms, wherein the heteroatoms that are optionally present are selected from the group consisting of N and O.

In compounds of structure $Q(Y_xZ_e)_b$ according to the invention or to be used according to the invention that can be synthesized with comparatively low effort Y is a structure element, containing a structure element or consisting of this, which is selected from the group consisting of

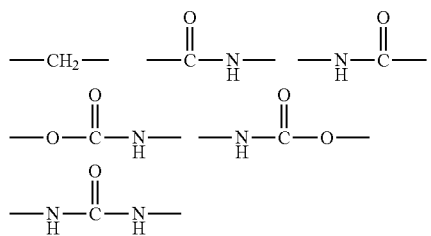

wherein in each case the bond arranged to the left of the graphic formula is closer to the structure element Q and the bond arranged on the right is closer to the structure element Z.

The compounds of structure $Q(Y_xZ_e)_b$ according to the invention or to be used according to the invention can be obtained by the preparation methods known to a person skilled in the art.

Compounds according to the invention or to be used according to the invention of structure $Q(Y_xZ_e)_b$ with an amide structure element can for example be obtained by reacting (i) an educt compound with an isocyanate group and (ii) an educt compound with a carboxylic acid group.

Compounds according to the invention or to be used according to the invention of structure $Q(Y_xZ_e)_b$ with a urethane structure element can for example be obtained by reacting (i) an educt compound with an isocyanate group and (ii) an educt compound with an alcohol group.

Compounds according to the invention or to be used according to the invention of structure $Q(Y_xZ_e)_b$ with a urea structure element can for example be obtained by reacting (i) an educt compound with an isocyanate group and (ii) an educt compound with an amino group.

Compounds according to the invention or to be used according to the invention of structure $Q(Y_xZ_e)_b$ with an allophanate structure element can for example be obtained by reacting (i) an educt compound with a urethane group and (ii) an educt compound with an isocyanate group.

Compounds according to the invention or to be used according to the invention of structure $Q(Y_xZ_e)_b$ with a biuret structure element can for example be obtained by reacting (i) an educt compound with a urea group and (ii) an educt compound with an isocyanate group.

Compounds according to the invention or to be used according to the invention of structure $Q(Y_xZ_e)_b$ with an N-acyl urea structure element can for example be obtained by reacting (i) an educt compound with an amide group and (ii) an educt compound with an isocyanate group.

In a preferred configuration of a lacquer composition according to the invention component (a1) is selected so that this comprises or consists of bis(methacrylolyoxymethyl)tricyclo[5.2.1.0$^{2,6}$]decane and/or bis(acrylolyoxymethyl)tricyclo [5.2.1.0$^{2,6}$]decane.

In lacquer compositions according to the invention methacrylic acid esters, because of their greater biocompatibility are preferred to the corresponding acrylic acid esters, i.e. the Z in compounds of structure $Q(YZ_e)_b$ (as defined above and wherein each Y is selected independently of any further structure elements Y or is omitted) preferably represents —O—(C=O)—C(CH$_3$)=CH$_2$.

Further preferred compounds (monomers) of structure $Q(YZ_e)_b$, (as defined above and wherein each Y is selected independently of any further structure elements Y or is omitted) of component (a1) are those with one, two, three, four or a plurality of functional groups selected from the group consisting of urethane, urea, N-acyl urea, allophanate, biuret and amide, wherein the amide function is not directly linked with an N atom, an O atom or a carbonyl group.

EP 1 238 993 describes a method for producing polyisocyanates containing acyl urea groups and mixtures of these and their use as starting components for the preparation of polyurethane synthetic materials.

EP 0 209 700 A2, DE 35 22 006 and DE 35 22 005 describe (meth)acrylic acid derivatives of certain tricyclodecenes with divalent bridge members from the group of urethanes or ureas, which can be used in the area of dentistry.

EP 0 000 194 A1 (corresponding to U.S. Pat. No. 4,160, 080) describes polyisocyanates, containing allophanate groups. These allophanate polyisocyanates may be used for the preparation of polyurethane foams, elastomers, duromers, coatings, adhesives and lacquers.

EP 0 682 012 B1 relates to a method for the preparation of bright-colored, light stable (cyclo-aliphatic) polyisocyanates comprising allophanate groups, by reacting organic compounds having urethane groups with organic polyisocyanates with (cyclo)aliphatically bonded isocyanate groups in the presence of tin(II) salts. The polyisocyanates described in EPO 682 012 B1 can be used as synthesis components in the preparation of polyurethane synthetic materials.

EP 1 727 846 B1 discloses a method for preparation of binding agents containing allophanate groups, containing groups reacting with ethylenically unsaturated compounds under polymerization under the effects of actinic radiation.

EP 0 712 840 B1 relates to a method for producing certain polyisocyanates containing allophanate groups through the reaction of compounds comprising urethane groups with the formation of allophanate. The compounds according to EP 0 712 840 B1 can be used as binding agents or binding agent components in coating media.

EP 0 867 457 B1 discloses an ethylenically unsaturated polyurethane, which is substantially free from isocyanate groups, which is the reaction product of an ethylenically unsaturated polyisocyanate, containing allophanate groups and β,γ-ethylenically unsaturated ether groups, with a hydroxyfunctional, ethylenically unsaturated compound, wherein the ethylenically unsaturated polyisocyanate is prepared by allophantization of the urethane groups-containing reaction products of an organic diisocyanate with a β,γ-ethylenically unsaturated ether alcohol, which is selected from the group consisting of glycerin diallyl ether, trimethylolpropane diallyl ether and pentaerythritriallyl ether. The ethylenically unsaturated polyurethanes with allophanate groups disclosed in EP 0 867 457 B1 can be used as binding agents in single component coating compositions.

DE 10 2007 040 240 A1 and EP 1 645 582 A1 in each case describe a method for preparation of radiation-curing allophanates through the reaction of compounds containing isocyanate groups and hydroxyfunctional compounds, wherein the ratio of NCO groups to OH groups is 1.45:1.0 through 1.1:1.0. According to DE 10 2007 040 239 A1 with the use of certain mixtures containing hydroxyethylacrylate and hydroxypropylacrylate as the hydroxyfunctional compounds corresponding radiation-curing allophanates are obtained. The radiation-curing allophanates according to these three documents can be used for the preparation of coatings and lacquers, as well as adhesives, inks, casting resins, dental compounds, release agents, photoresists, stereolithography systems, resins for composites and sealants.

DE 10 2004 060 285 A1 relates to radiation-curable compounds based on a dicidol mixture (containing two or three isomers 3,8-, 4,8- and/or 5,8-bis(hydroxymethyl)tricyclo[5.2.1.0$^{2,6}$]decane) with at least one compound, having at least one ethylenically unsaturated grouping with simultaneously at least one reactive grouping in relation to dicidol, wherein this compound may be a reaction product of hydroxyalkyl(meth)acrylate and diisocyanate. The compositions according to DE 10 2004 060 285 A1 can be used as radiation-induced-curing coating materials, adhesives, laminations, printing and other inks, polishes, varnishes, pigment pastes, fillers, cosmetic materials, packaging materials and/or sealing and/or insulating materials.

WO 2006/063891 A1 discloses radically polymerizable compounds, substantially containing the reaction product of a dicidol mixture and at least one compound, which has at least one ethylenically unsaturated grouping with simultaneously at least one reactive grouping in relation to dicidol. The areas of application correspond to those mentioned in DE 10 2004 060 285 A1.

WO 03/035013 A1 and DE 602 16 951 T2 relate to dental adhesive compositions for binding of dental restoration means to dentin and/or tooth enamel. In these documents inter alia the preparation of 3,(4),8,(9)-bis(2-propenamidomethyl)tricyclo[5.2.1.0]$^{2,6}$-decane is described.

U.S. Pat. No. 6,670,499 B1 describes diurethanes derived from adamantane. The compounds described in U.S. Pat. No. 6,670,499 are suitable as intermediate products for use in dentistry or for producing optical materials (such as lenses, for example).

In the area of dental engineering there is a constant need for more low-shrinkage radically polymerizable monomers. Thus a further object for the present invention was to provide novel, radically polymerizable monomers, which in a lacquer composition according to the invention, in particular in a dental lacquer composition according to the invention, can be used as a constituent of component (a1).

This further object is achieved by a compound of structure $Q(YZ_e)_b$ (as defined above and wherein each Y is selected independently of any further structure elements Y) with one, two, three, four or a plurality of functional groups selected from the group consisting of N-acyl urea, allophanate, biuret and amide, wherein the amide function is not directly linked with an N atom, an O atom or a carbonyl group, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups;

b is an integer selected from the group of integers 2, 3, 4;
each Z represents a structure element, which independently of any further structure elements Z is selected from the group consisting of
—O—(C=O)—CH=CH$_2$, —O—(C=O)—C(CH$_3$)=CH$_2$, —(C=O)—CH=CH$_2$ and —(C=O)—C(CH$_3$)=CH$_2$, —CH=CH$_2$, —C(CH$_3$)=CH$_2$ and —O—CH=CH$_2$, each index e is an integer, which independently of any further indices e is selected from the group of integers 1, 2, 3 and 4;

each Y represents a structure element, which in the structure $Q(YZ_e)_b$ bonds the polyalicyclic structure element Q with e structure elements Z;

wherein the compound is a first reaction product of a first reaction of

A) a compound of structure $QG_b$, in which each G represents a reactive group, which independently of further groups G is selected from the group consisting of (—CH$_2$)$_n$—NH$_2$, (—CH$_2$)$_n$—(OCH$_2$—CHR)$_m$—OH, (—CH$_2$)$_n$—NCO and (—CH$_2$)$_n$—COOH with B) two or a plurality of identical or different compounds MZ$_e$, wherein M represents a structure element which in each case has one or a plurality of grouping(s) that react with the groups G selected from the group consisting of —NH, —NH$_2$, —OH, —NCO and —COON, wherein the following applies:
R, in each case independently of any further R, represents a hydrogen atom or an alkyl radical; preferably R represents a hydrogen atom or a linear or branched alkyl radical with 1 through 6 C atoms; more preferably R represents a hydrogen atom or a methyl radical;

m is an integer selected from the group of integers from 0 through 10, each index n is an integer, which independently of any further indices n is selected from the group consisting of 0 and 1, or the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the first and/or second reaction.

From that stated above it can be inferred that for compounds according to the invention, containing an amide group (as defined) this amide group is not a constituent of the urethane group.

Further preferred are compounds according to the invention of structure $Q(YZ_e)_b$ (as defined above and wherein each Y is selected independently of any further structure elements Y) of component (a1) with one, two, three, four or a plurality of functional groups selected from the group consisting of N-acyl urea, allophanate, biuret and amide, wherein the amide function is not directly linked with an N atom, an O atom or a carbonyl group, wherein the amide in turn preferably represents (meth)acrylamide.

In preferred compounds according to the invention of structure $Q(YZ_e)_b$ (as defined above and wherein each Y is selected independently of any further structure elements Y), the linking between Q and at least one structure element Z takes place via a bridge which contains or comprises a divalent bridge member, selected from the group consisting of

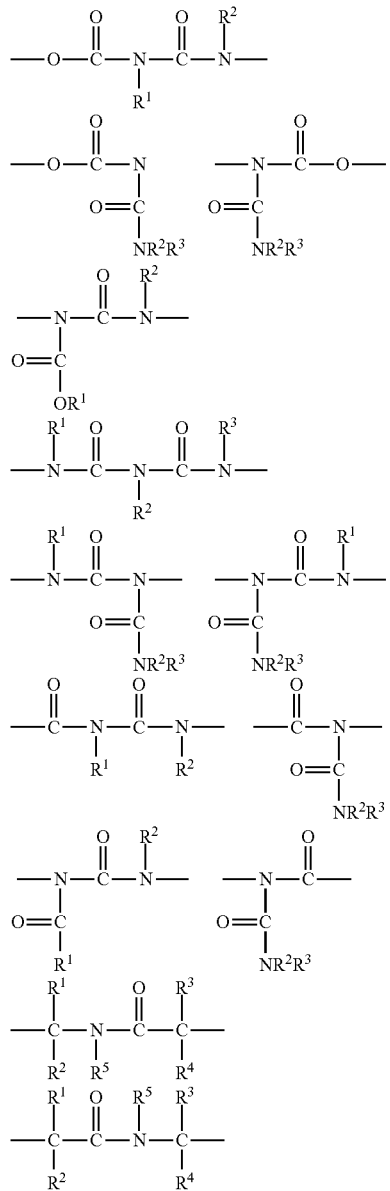

wherein $R^1$, $R^2$, $R^3$, $R^4$, $R^5$ represent other radicals of the compound, wherein in each case the bond arranged to the left of the graphic formula is closer to the structure element Q and the bond arranged on the right is closer to the structure element Z.

The further object is likewise achieved by novel compounds of structure $Q(Y_xZ_e)_b$ with x=1 with one, two, three, four or a plurality of functional groups that are selected from the group consisting of N-acyl urea, allophanate and biuret, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element Q not substituted by substituents $YZ_e$ is or are substituted by alkyl groups, alkoxy groups, halogen atoms or trifluormethyl groups;

b is an integer selected from the group of integers 2, 3, 4;

each Z represents a structure element, which independently of any further structure elements Z is selected from the group consisting of
—O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$ and —O—CH=CH$_2$, each index e is an integer, which independently of any further indices e is selected from the group of integers 1, 2, 3 and 4;

each Y represents a structure element that in the structure $Q(Y_xZ_e)_b$ with x=1 links the polyalicyclic structure element Q with e structure elements Z and contains or consists of a structure element selected from the group consisting of

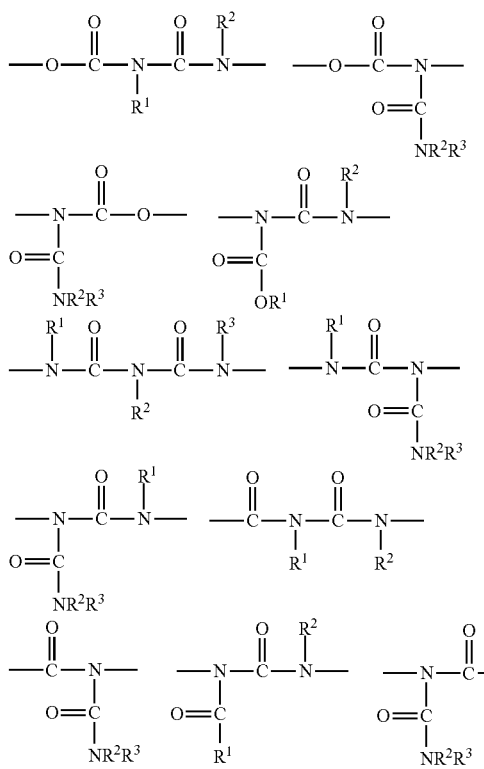

wherein $R^1$, $R^2$, and $R^3$ represent other radicals of the compound, wherein in each case the bond arranged to the left of the graphic formula is closer to the structure element Q and the bond arranged on the right is closer to the structure element Z.

These compounds according to the invention are eminently suitable as monomers for use in lacquer compositions according to the invention.

Preferably such a compound according to the invention of structure $Q(Y_xZ_e)_b$ with x=1 comprises two, three, four or a plurality of functional groups selected from the group consisting of N-acyl urea, allophanate and biuret.

In a preferred configuration each index e represents an integer, which independently of any further indices e is selected from the group of integers 2, 3 and 4.

The above-mentioned radicals $R^1$, $R^2$ or $R^3$ of a novel compound according to the invention are, in each case independently of one another, preferably selected from the group consisting of hydrogen, linear, branched or ring-comprising structure elements with 1 through 30 C atoms and 0 through 10 heteroatoms, wherein the heteroatoms that are optionally present are preferably selected from the group consisting of N and O.

The other radicals $R^1$, $R^2$ or $R^3$ of a novel compound according to the invention are, in each case independently of one another, preferably selected from the group consisting of hydrogen, linear, branched or ring-comprising structure elements with 1 through 30 C atoms and 0 through 10 heteroatoms, wherein the heteroatoms that are optionally present are preferably selected from the group consisting of N and O.

The other radicals $R^1$, $R^2$ or $R^3$ of a novel compound according to the invention are, in each case independently of one another, preferably selected from the group consisting of hydrogen, linear, branched or ring-comprising structure elements with 1 through 20 C atoms and 0 through 5 heteroatoms, wherein the heteroatoms that are optionally present are selected from the group consisting of N and O.

A novel compound according to the invention $Q(Y_xZ_e)_b$ with x=1, preferably a compound according to the invention $Q(Y_xZ_e)_b$ with x=1 as identified above as preferred, can preferably be prepared by reacting a first reaction product, which is the reaction product of a first reaction of A) a compound of structure $QG_b$, in which each G represents a reactive group, which independently of further groups G is selected from the group consisting of $(-CH_2)_n-NH_2$, $(-CH_2)_n-(OCH_2-CHR)_m-OH$, $(-CH_2)_n-NCO$ and $(-CH_2)_n-COOH$ with B) two or a plurality of identical or different compounds $MZ_e$, wherein M represents a structure element which in each case has one or a plurality of grouping(s) that react with the groups G selected from the group consisting of —NH, —NH$_2$, —OH, —NCO and —COON, wherein the following applies:

R in each case independently of any other R represents a hydrogen atom or an alkyl radical;

m is an integer selected from the group of integers from 0 through 10, each index n is an integer, which independently of any further indices n is selected from the group consisting of 0 and 1, wherein the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the first and/or second reaction.

A compound according to the invention in a preferred configuration is a second reaction product from a reaction of the above first reaction product with C) a further compound according to A) or B), wherein each further compound according to A) or B) has the same meaning as in the first reaction, and/or wherein the compound is a third reaction product from a reaction of the above second reaction product with D) a further compound according to A) or B), wherein each further compound according to A) or B) has the same meaning as in the first and/or the second reaction, preferably as in the first and the second reaction.

In a first embodiment m=0. This applies to all aspects of the present invention.

In preferred compounds according to the invention the link between Q and at least one structure element Z takes place via a bridge which contains or consists of a divalent bridge member, selected from the group consisting of

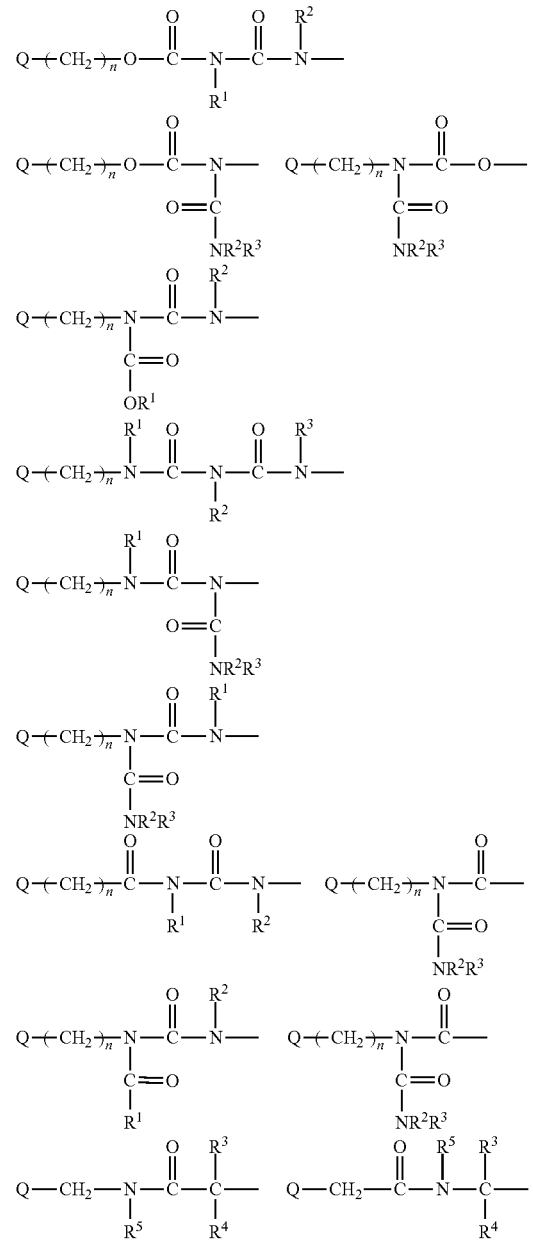

wherein $R^1$, $R^2$, $R^3$ $R^4$, $R^5$ represent other radicals of the compound and Q and n have the meaning indicated above.

The bond shown on the right of each graphic formula is closest to the structure element Z.

In a preferred configuration a novel compound according to the invention $Q(Y_xZ_e)_b$ with x=1, preferably a compound according to the invention $Q(Y_xZ_e)_b$ with x=1 as identified above or below as preferred, comprises one or a plurality of structure elements selected from the group consisting of

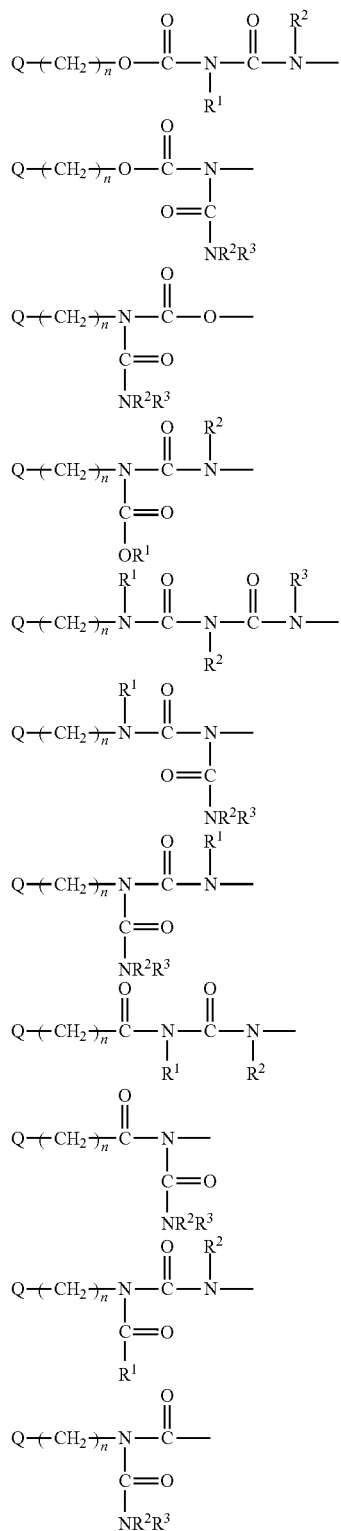

wherein $R^1$, $R^2$ and $R^3$ represent other radicals of the compound (and preferably have the abovementioned preferred meaning) and Q has the above-mentioned meaning and the index n is selected from the group consisting of 0 and 1.

As already mentioned above preferred novel compounds according to the invention are those wherein Q represents a saturated polyalicyclic structure element, selected from the group consisting of bicyclic and tricyclic hydrocarbon radicals, wherein preferably none of the hydrogen atoms of this polyalicyclic structure element Q not substituted by $YZ_e$ (wherein each Y is selected independently of any further structure elements Y) substituents is substituted.

Particularly preferred compounds according to the invention are those wherein the structure element Q represents a tricyclo[$5.2.1.0^{2,6}$]decane radical, a tricyclo[$5.2.1.0^{2,6}$]dec-3-ene radical, a tricyclo[$3.3.1.1^{3,7}$]decane radical or a bicyclo[2.2.1]heptane radical.

Preference is for novel compounds according to the invention in which
(i) the structure element Z represents —O—(C=O)—C($CH_3$)=$CH_2$, wherein the functional groups are allophanate, biuret or acyl urea groups, since with these compounds particularly good results have been obtained, and/or
(ii) the structure element Q represents a tricyclo[$5.2.1.0^{2,6}$]decane radical.

Further preference is for novel compounds according to the invention, in which the structure element Z represents —O—(C=O)—C($CH_3$)=$CH_2$, wherein the functional groups are allophanate, biuret or acyl urea groups and the structure element Q represents a tricyclo[$5.2.1.0^{2,6}$]decane radical.

Preference is for novel compounds according to the invention in which all photocurable groups present correspond to the structure element Z.

Preference is for novel compounds according to the invention in which all terminal polymerizable groups present correspond to the structure element Z.

A novel compound according to the invention, apart from photocurable groups of the structure element Z, can also comprise further polymerizable, preferably terminal polymerizable groups, which are not photocurable, in particular not under the normal conditions that exist in dentistry. This is generally not preferred, however, since such groups do not contribute towards the desired characteristics of the product that exists following polymerization.

Further preferred novel compounds according to the invention are those in which at least one structure element $YZ_e$ is selected independently of the further structure elements $YZ_e$, and preferably all structure elements $YZ_e$ are selected from the group consisting of

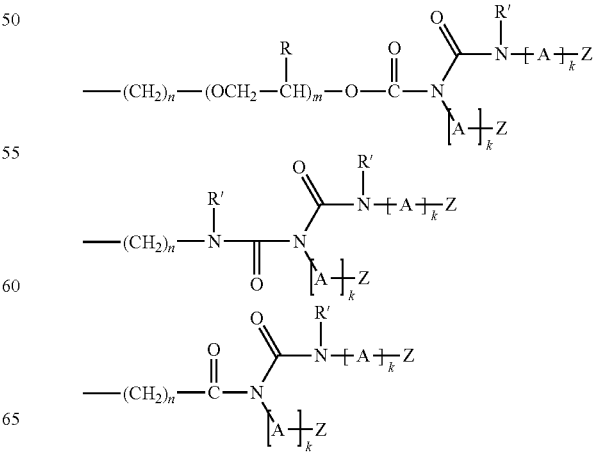

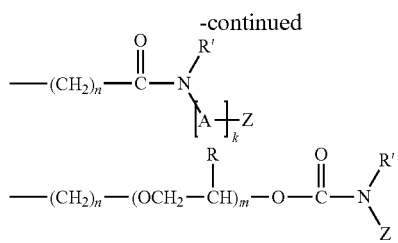

wherein Z, R, m and n have the meaning given above and wherein the following also applies:
each A represents a divalent organic bridge member,
each index k is an integer, which independently of any further indices k is selected from the group consisting of 0 and 1;
each R' represents a structure element which independently of any further structure elements R' is selected from the group consisting of H and a structure element (C=O)—NH-(A)$_k$-Z, wherein A, Z and k in turn have the meanings given above.

In a preferred embodiment m=0.

Similarly preferred compounds according to the invention are those in which at least one structure element $YZ_e$ is selected independently of the further structure elements $YZ_e$, and preferably all structure elements $YZ_e$ are selected from the group consisting of

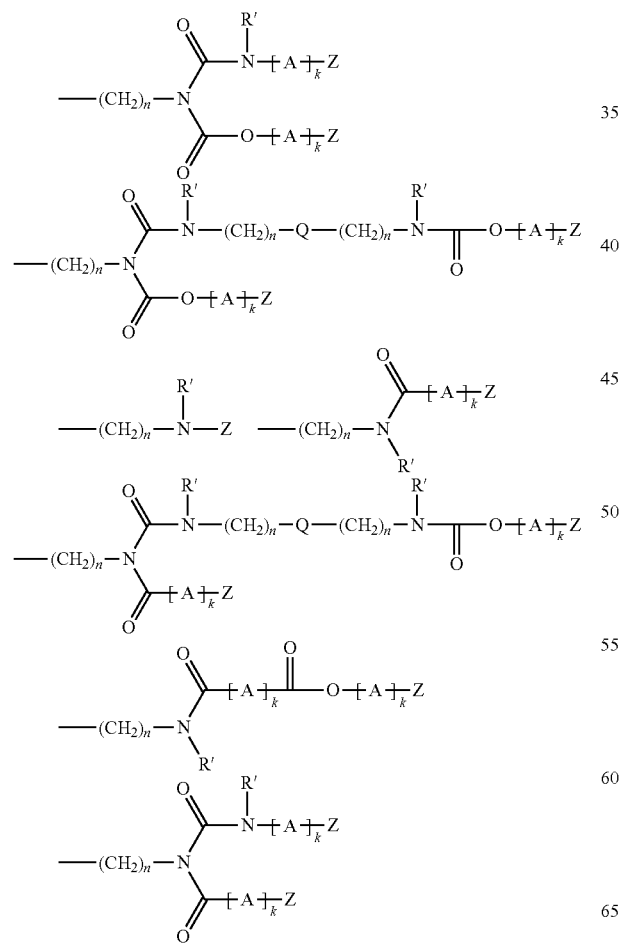

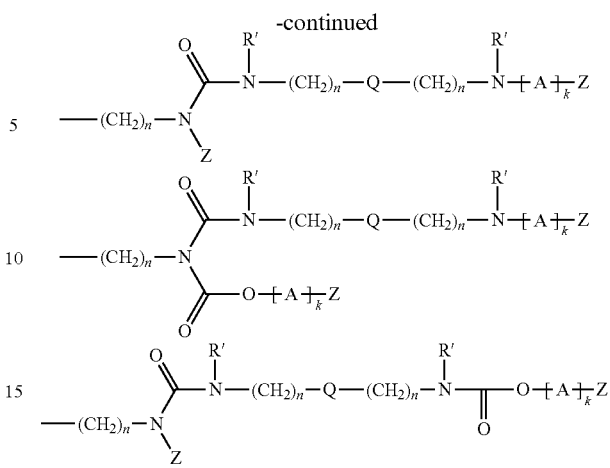

wherein each Q independently of any further structure elements Q has the above meaning and wherein Z, A, k and R', as well as n, have the above meaning.

In a preferred configuration the present invention relates to a compound according to the invention $Q(Y_xZ_e)_b$ with x=1, preferably a compound according to the invention $Q(Y_xZ_e)_b$ with x=1 as identified above or below as preferred, wherein at least one structure element $YZ_e$ is selected independently of the further structure element(s) $YZ_e$, and preferably all structure elements $YZ_e$ are selected from the group consisting of

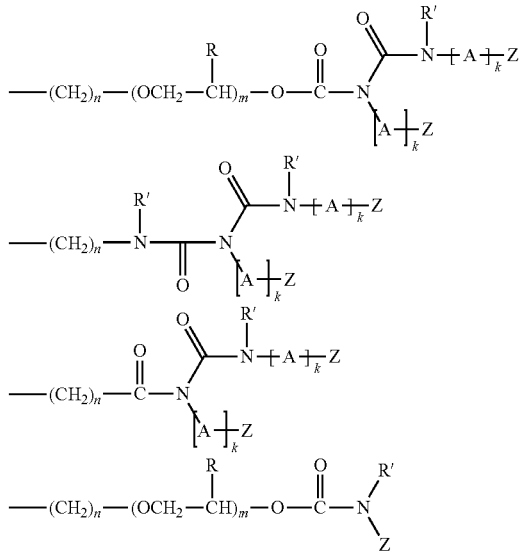

wherein Z, R, m and n have the meaning given above and wherein the following also applies:
each A represents an organic structure element,
each index k is an integer, which independently of any further indices k is selected from the group consisting of 0 and 1;
each R' represents a structure element which independently of any further structure elements R' is selected from the group consisting of H and a structure element (C=O)—NH-(A)$_k$-Z, wherein A, Z and k in turn have the meanings given above.

In a preferred configuration the present invention relates to a novel compound according to the invention $Q(Y_xZ_e)_b$ with x=1, preferably a compound according to the invention $Q(Y_x$-$Z_e)_b$ with x=1 as identified above or below as preferred, wherein
at least one structure element $YZ_e$ is selected independently of the further structure element(s) $YZ_e$, and preferably all structure elements $YZ_e$ are selected
from the group consisting of

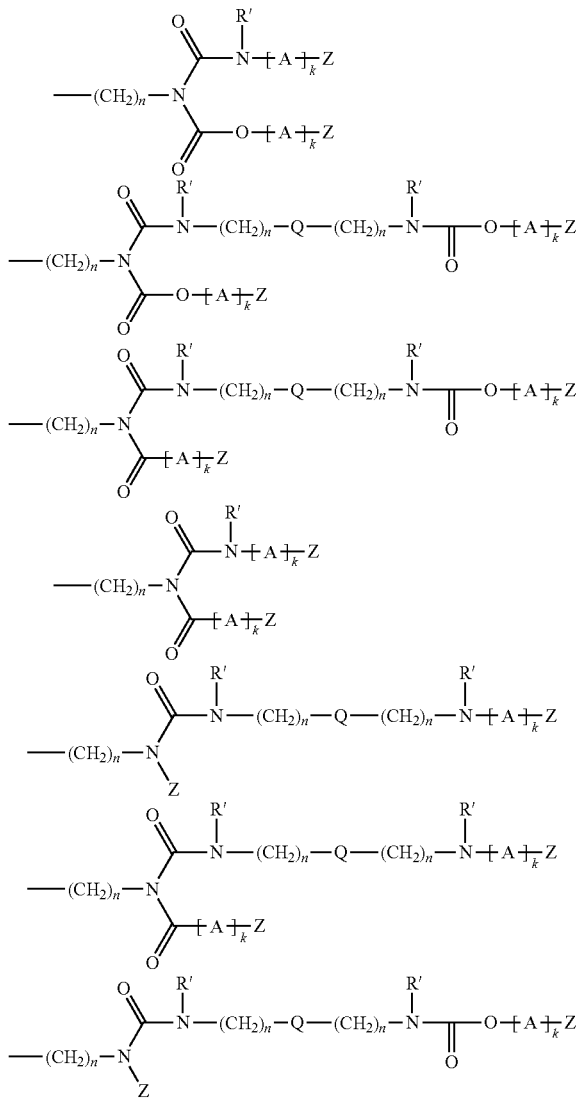

wherein each Q independently of any further structure elements Q has the above meaning, and
wherein Z and n have the above-mentioned meaning and wherein the following also applies:
  each A represents an organic structure element,
  each index k is an integer, which independently of any further indices k is selected from the group consisting of 0 and 1;
  each R' represents a structure element which independently of any further structure elements R' is selected from the group consisting of H and a structure element (C=O)—NH-$(A)_k$-Z, wherein A, Z and k in turn have the meanings given above.
Here in turn preference is for compounds to be used according to the invention in which each structure element A independently of any, further structure elements A is selected from the group consisting of all linear, branched or ring-comprising divalent organic bridge members with 1 through 25 C atoms and optionally 1 through 10, preferably 1 through 5 heteroatoms, wherein the heteroatoms that are optionally present are preferably selected from the group consisting of N and O.

Here in turn preference is for a compound according to the invention in which each structure element A independently of any further structure elements A is selected from the group consisting of linear, branched or ring-comprising structure elements with 1 through 25 C atoms and 0 through 10 heteroatoms, preferably with 1 through 5 heteroatoms, wherein the heteroatoms that are optionally present are preferably selected from the group consisting of N and O.

Further preference is for compounds in which each structure element A independently of any further structure elements A is selected from the group consisting of $(C_1$-$C_{20})$ alkylene, $(C_1$-$C_{20})$ heteroalkylene, $(C_3$-$C_{20})$ cycloalkylene, $(C_4$-$C_{20})$ cycloalkylalkylene, $(C_2$-$C_{20})$ alkenylene, $(C_3$-$C_{20})$ cycloalkenylene, $CC_4$-$C_{20})$ cycloalkenylalkylene, $(C_4$-$C_{20})$ cycloalkenylenalkylene, $(C_3$-$C_{25})$ arylene, $(C_2$-$C_{25})$ heteroarylene, $(C_4$-$C_{25})$ arylalkylene, $C_4$-$C_{25})$ arylenalkylene, $(C_4$-$C_{25})$ arylheteroalkylene, and $(C_4$-$C_{25})$ arylenheteroalkylene.

In preferred configurations structure element A comprises one or a plurality of the following atoms or groups of atoms: —O—, —O—$Ar^1$—$CR^6R^7$—$Ar^2$—O—, —$NR^8$—, —N—(C=O)—, —NH—(C=O)—O—, —NH—C(=O)—N—
wherein the following applies:
$Ar^1$ and $Ar^2$ independently of each other represent an aromatic ring which is optionally substituted, here preferably once or a plurality of times substituted with $C_1$-$C_4$-alkyl radicals, here in turn preferably a phenyl ring,
$R^6$, $R^7$ and $R^8$ independently of one another represent hydrogen or a C1-C8 radical, here preferably a C1-C4 alkyl radical, here in turn preferably methyl or ethyl.

The present invention further relates to a method for preparing a compound according to the invention $Q(YZ_e)_b$ (wherein each Y is selected independently of any further structure elements Y) or a mixture, comprising at least such a compound according to the invention $Q(YZ_e)_b$, with the following steps:
In a first reaction, reacting
A) a compound of structure $QG_b$, in which each G represents a reactive group, which is selected independently of further G groups from the group consisting of (—$CH_2)_n$—$NH_2$, (—$CH_2)_n$—(OCH$_2$—CHR)$_m$—OH, (—$CH_2)_n$—NCO and (—$CH_2)_n$—COOH, preferably a compound of structure $QG_b$, in which each G stands for a reactive group, which is selected independently of further G groups from the group consisting of —$NH_2$, —$CH_2NH_2$, —OH, —$CH_2OH$, —NCO, —$CH_2NCO$, and —COOH,
with
B) two or a plurality of identical or different compounds $MZ_e$, wherein M represents a structure element which in each case has one or a plurality of grouping(s) that react with the groups G selected from the group consisting of —NH, —$NH_2$, —OH, —NCO and —COOH
to form a first reaction product,
optionally in a second reaction, reacting the first reaction product with
C) a further compound according to A) or B), wherein each further compound according to A) or B) has the above meaning, independently of what A) and/or B) represent in the first reaction, to form a second reaction product,
and optionally in a third reaction, reacting the second reaction product with
D) a further compound according to A) or B), wherein each further compound according to A) or B) has the above meaning, independently of what A) and/or B) represent in the first and/or second reaction.

wherein Q, b, Y, Z, and e in each case have the above meanings, and wherein the following applies:
R, in each case independently of any other R, represents a hydrogen atom or an alkyl radical; preferably R represents a hydrogen atom or a linear or branched alkyl radical with 1 through 6 C atoms; more preferably R represents a hydrogen atom or a methyl radical;
m is an integer selected from the group of integers from 0 through 10,
each index n is an integer, which independently of any further indices n is selected from the group consisting of 0 and 1,
wherein the ratio of the total number of NCO groups to the total number of $-NH_2$, $-OH$ and $-COOH$ in the total number of compounds according to A) and B) in the first, optional second and optional third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

A preferred method according to the invention for preparation of a compound according to the invention $Q(Y_xZ_e)_b$ with x=1, preferably a compound according to the invention $Q(Y_xZ_e)_b$ with x=1 identified above or below as preferred, or a mixture comprising at least one such compound $Q(Y_xZ_e)_b$ is a method with the following steps:
In a first reaction, reacting
A) a compound of structure $QG_b$, in which each G represents a reactive group, which independently of further groups G is selected from the group consisting of $(-CH_2)_n-NH_2$, $(-CH_2)_n-(OCH_2-CHR)_m-OH$, $(-CH_2)_n-NCO$ and $(-CH_2)_n-COOH$
with
B) two or a plurality of identical or different compounds $MZ_e$, wherein M represents a structure element which in each case has one or a plurality of grouping(s) that react with the groups G selected from the group consisting of $-NH$, $-NH_2$, $-OH$, $-NCO$ and $-COOH$
to form a first reaction product,
in a second reaction, reacting the first reaction product with
C) a further compound according to A) or B), wherein each further compound according to A) or B) has the above meaning, independently of what A) and/or B) represent in the first reaction,
to form a second reaction product,
and optionally in a third reaction, reacting the second reaction product with
D) a further compound according to A) or B), wherein each further compound according to A) or B) has the above meaning, independently of what A) and/or B) represent in the first and/or second reaction.

wherein Q, b, Y, Z, e, M, R, m and n in each case have the above meanings, and
wherein the ratio of the total number of NCO groups to the total number of $-NH_2$, $-OH$ and $-COOH$ in the total number of compounds according to A) and B) in the first, second and optional third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

In a method according to the invention for preparation of a compound according to the invention $Q(Y_xZ_e)_b$ with x=1, preferably a compound according to the invention $Q(Y_xZ_e)_b$ with x=1 identified above or below as preferred, or a mixture comprising at least one such compound $Q(Y_xZ_e)_b$, the ratio of the total number of NCO groups reacted to the total number of $-NH_2$, $-OH$ and $-COOH$ reacted in the total number of compounds according to A) and B) in the first, second and optional third reaction is preferably in the range 1.1:1 through 5:1, more preferably in the range 1.25:1 through 4:1, particularly preferably in the range 1.5:1 through 3:1, and most preferably in the range 2:1 through 2.5:1.

Preferably the reaction to the first reaction product, to the second reaction product and/or to the third reaction product takes place in the presence of a catalyst.

Preferred catalysts here are tertiary amines or Lewis acids, here in turn preference is for metal salts of higher fatty acids, particularly dibutyltin dilaurate or tin (II) octoate The quantity of catalyst here is preferably in the range 0.01 through 2 wt. %, preferably 0.08 through 1 wt. %, in relation to the total quantity of reactants according to A) and B) and optionally C) and optionally D).

The reaction to the first reaction product, to the second reaction product and/or the third reaction product preferably takes place in a temperature range of 0 through 160° C., preferably in the range 30 through 140° C. and particularly preferably in the range 60 through 120° C. The reaction is preferably carried out at normal pressure (1013 mbar).

In a further aspect the present invention relates to a mixture comprising one, two or a plurality of different compounds according to the invention preparable using a method according to the invention.

In a further aspect the present invention relates to the use of a lacquer composition according to the invention, preferably in one of the configurations identified as preferred or particularly preferred, for coating a surface, in particular as a protective and/or gloss lacquer.

In a further aspect the present invention relates to the use of a compound according to the invention, preferably in one of the configurations identified as preferred or particularly preferred, for the preparation of a lacquer composition, preferably for the preparation of a dental lacquer composition according to the invention.

In a further aspect the present invention relates to the use of a compound according to the invention, preferably in one of the configurations identified as preferred or particularly preferred, in a lacquer composition, preferably in one of the configurations identified as preferred or particularly preferred.

In a further aspect the present invention relates to the use of a compound according to the invention, preferably in one of the configurations identified as preferred or particularly preferred, in a dental lacquer composition.

In a further aspect the present invention relates to a lacquer composition as or for use as a dental material, preferably as a cavity and/or surface lacquer, as an underfilling for dental filling materials, to protect the tooth enamel, to prevent caries, to protect a restoration (in particular from premature attrition), to improve the resistance to abrasion of a dental filling material, to stabilize restored surfaces, to protect against abrasion and/or discoloration of a tooth or a restoration, to close marginal gaps and/or microcracks, to smooth restored surfaces, to provide a natural sheen to a tooth or restoration and to reduce deposits of coloring matter on a tooth or a restoration.

The present invention also relates to a product, obtainable by curing of a lacquer composition according to the invention, in particular in one of the configurations identified as particularly preferred.

The present invention thus also relates to a lacquer composition, preferably in one of the configurations identified above or below as preferred, for use in a therapeutic method as a dental material, preferably as a cavity and/or surface lacquer, as an underlining for dental filling materials, to protect the tooth enamel, to prevent caries, to protect a restoration (particularly from premature attrition), to improve the resistance to abrasion of a dental filling material, to stabilize restored surfaces, to protect against abrasion and/or discoloration of a tooth or a restoration, to close marginal gaps and/or microcracks, to smooth restored surfaces, to provide a natural sheen to a tooth or restoration and to reduce deposits of coloring matter on a tooth or a restoration.

The method can include providing the lacquer composition as described herein and applying the lacquer composition to a surface, such as tissue of a patient. The method can be part a medical procedure, e.g., a dental procedure. The method can include applying the lacquer composition as a dental material, preferably as a cavity and/or surface lacquer, as an underfilling for dental filling materials, to protect the tooth enamel, to prevent caries, to protect a restoration (particularly from premature attrition), to improve the resistance to abrasion of a dental filling material, to stabilize restored surfaces, to protect against abrasion and/or discoloration of a tooth or a restoration, to close marginal gaps and/or microcracks, to smooth restored surfaces, to provide a natural sheen to a tooth or restoration and to reduce deposits of coloring matter on a tooth or a restoration. The method can further include curing the lacquer composition. As used herein, "tissue" is intended to have its conventional meaning and include all features of teeth.

The present invention also relates to the non-therapeutic use, preferably the cosmetic or aesthetic use, of a lacquer composition according to the invention, preferably in one of the configurations identified above or below as preferred, to smooth restored surfaces, to provide a natural sheen to a tooth or restoration and to reduce deposits of coloring matter on a tooth or a restoration.

Accordingly the present invention also relates to the use of a lacquer composition according to the invention, preferably in one of the configurations identified above or below as preferred, in a non-therapeutic method, preferably in a cosmetic or aesthetic method, to smooth restored surfaces, to provide a natural sheen to a tooth or restoration and to reduce deposits of coloring matter on a tooth or a restoration.

For the preparation of the compounds according to the invention preferably hydroxyl compounds of (meth)acrylates can be used, wherein mixtures of acrylates and methacrylates can also be used. Preference (for use as reaction partners according to components B), C) and/or D)) is for:
alkylene oxide mono(meth)acrylates such as for example ethylene glycol mono(meth)acrylate, diethylene glycol mono (meth)acrylate, triethylene glycol mono(meth)acrylate, tetraethylene glycol mono(meth)acrylate, etc., polyalkylene oxide mono(meth)acrylates such as for example polyethylene glycol mono(meth)acrylate, polypropylene glycol mono(meth)acrylate, polybutylene glycol mono(meth) acrylate, etc., hydroxyalkyl mono(meth)acrylates such as for example hydroxyethyl(meth)acrylate, hydroxypropyl (meth)acrylate, 2-hydroxypropyl(meth)acrylate, hydroxybutyl(meth)acrylate, 4-hydroxybutyl(meth)acrylate, hydroxypentyl(meth)acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth) acrylate, hydroxyundecyl(meth)acrylate, hydroxydodecyl (meth)acrylate, etc., poly($\epsilon$-caprolactone)mono(meth) acrylate, poly($\gamma$-caprolactone)mono(meth)acrylate, etc., the mono-, di-, tetra-, or penta(meth)acrylates of polyhydric alcohols, such as glycerin, such as for example glycerin di(meth)acrylate (2-hydroxypropyl-1,3-di(meth)acrylate, 3-hydroxypropyl-1,2-di(meth)acrylate), such as trimethylolpropane, such as for example trimethylolpropane di(meth)acrylate, such as pentaerythritol, such as for example pentaerythritoltri(meth)acrylate, such as dipentaerythritol, such as for example dipentaerythritolpenta(meth)acrylate, such as ditrimethylolpropantri(meth)acrylate, such as neopentyl glycol(meth)acrylate, the (meth) acrylates of alkoxylated or phenoxylated glycerin, here preferably the (meth)acrylates of ethoxylated, propoxylated, etc. glycerin, trimethylolpropane, pentaerythritol, dipentaerythritol, ditrimethylolpropane, etc. and the technical mixtures thereof, bisphenol-A-glycidyl-(meth)acrylate (Bis-GMA), bisphenol-B-glycidyl-(meth)acrylate, bisphenol-C-glycidyl-(meth)acrylate, bisphenol-F-glycidyl-(meth)acrylate, alkoxylated bisphenol-A-glycidyl-(meth)acrylate (e.g. ethoxylated bisphenol-A-glycidyl-(meth)acrylate), etc.

For the preparation of the compounds according to the invention as component B) isocyanates can also be used. Preference here is for mono- and diisocyanates.

Preferred diisocyanates are selected from the group consisting of cyclohexane diisocyanate, methylcyclohexane diisocyanate, ethylcyclohexane diisocyanate, propylcyclohexane diisocyanate, methyldiethylcyclohexane diisocyanate, phenylene diisocyanate, toluoylene diisocyanate, bis(isocyanatophenyl)methane, propane diisocyanate, butane diisocyanate, pentane diisocyanate, hexane diisocyanate, such as hexamethylene diisocyanate or 1,5-diisocyanato-2-methyl pentane, heptane diisocyanate, octane diisocyanate, nonane diisocyanate, such as 1,6-diisocyanato-2,4,4-trimethylhexane or 1,6-diisocyanato-2,2,4-trimethylhexane, nonane triisocyanate, such as 4-isocyanatomethyl-1,8-octane diisocyanate, decane di- and triisocyanate, undecane di- and -triisocyanate, dodecandi- and -triisocyanates, isophorone diisocyanate, dicyclohexylmethane-4,4'-diisocyanate, isocyanatomethylmethylcyclohexyl isocyanate, 1,3-bis(isocyanatomethyl)cyclohexane or 1,4-bis(isocyanatomethyl) cyclohexane.

Preferred monoisocyanates are (meth)acryloyl isocyanate and (meth)acryl-C2-C8-alkyl isocyanates (e.g. (meth)acrylalkyl isocyanates with alkyl spacers, having 2 through 8, particularly preferably 2 through 6 carbon atoms), here in turn preference is for (meth)acryl ethyl isocyanate (2-isocyanatoethyl(meth)acrylate).

Furthermore, as component B) monoisocyanates have proven to be an advantage that are the reaction products of amino- or hydroxyalkyl(meth)acrylates, the alkyl spacers of which have 1 through 12, preferably 2 through 8, particularly preferred 2 through 6 carbon atoms, and diisocyanates.

Preferably to this end a diisocyanate mentioned above is reacted in equimolar proportions with an amino- or hydroxylalkyl compound (indicated above as preferred) of a (meth) acrylate, wherein the hydroxylalkyl compounds in turn are preferably selected from the group consisting of hydroxyethyl(meth)acrylate, hydroxypropyl(meth)acrylate, hydroxybutyl(meth)acrylate, hydroxypentyl(meth)acrylate and hydroxyhexyl(meth)acrylate.

Quoted examples are the reaction products in the molar ratio of 1:1 of hydroxyethylmethacrylate and isophorone diisocyanate, dicyclohexylmethane-4,4'-diisocyanate or hexamethylene diisocyanate.

In the following the invention is initially explained in detail for monomers comprising tricyclic structure elements Q using the example of tricyclo[5.2.1.0$^{2,6}$]decane (TCD) through derivatives.

1.) Starting with the bis(hydroxymethyl)tricyclo[5.2.1.0$^{2,6}$] decane (TCD-diol)
bis(hydroxynnethyl)tricyclo[5.2.1.0$^{2,6}$]decane is commercially available, for example as a dicidol mixture of the isomeric compounds 3,8-bis(hydroxymethyl)tricyclo [5.2.1.0$^{2,6}$]decane and 4,8-bis(hydroxymethyl)tricyclo [5.2.1.0$^{2,6}$]decane as well as 3,9-bis(hydroxymethyl)tricyclo[5.2.1.0$^{2,6}$]decane and 4,9-bis(hydroxymethyl)tricyclo [5.2.1.0$^{2,6}$]decane.

The bis(hydroxymethyl)tricyclo[5.2.1.0$^{2,6}$]decanes can, starting with dicyclopentadiene (tricyclo[5.2.1.0$^{2,6}$]deca-3,8-diene), be synthesized. Dicyclopentadiene is easily accessible in a Diels-Alder reaction by dimerization of cyclopentadiene. Hydroformylation of dicyclopentadiene then produces the bis(hydroxymethyl)tricyclo[5.2.1.0$^{2,6}$]decane. According to the synthesis route taken bis(hydroxymethyl) tricyclo[5.2.1.0$^{2,6}$]decanes specifically substituted at different positions can be obtained. Thus in published documents JP 7-206740, EP 1 112 995 B1 or EP 0 049 631 B1 specifications are provided on how, for example, the 8,9-bis(hydroxymethyl)tricyclo[5.2.1.0$^{2,6}$]decane is preparable. DE 103 52 260 B3 on the other hand describes a method for preparing 3(4), 8(9)-bis(hydroxymethyl)tricyclo[5.2.1.0$^{2,6}$] decane. The notation of the positions of the hydroxymethyl groups 3(4), 8(9) means 3 or 4, 8 or 9.

The commercially available starting compound that can be used for the preparation of monomers according to the invention, bis(hydroxymethyl)tricyclo[5.2.1.0$^{2,6}$]decane, thus contains hydroxymethyl groups both at positions 3 or 4 and in positions 8 or 9. It is now possible by addition of alkylene oxides, in general in quantities of 1 through 10 mol, in particular of ethylene oxide, propylene oxide, butylene oxide, etc. in the presence of basic catalysts and according to known methods to synthesize the corresponding polyether polyols. EP0023686 B1 contains more detailed preparation specifications in this connection.

The reaction of the 3(4), 8(9)-bis(hydroxymethyl)tricyclo [5.2.1.0$^{2,6}$]decanes with isocyanates to form the corresponding urethanes is likewise known. Thus DE 3522006 A1 describes the reaction of the 3(4), 8(9)-bis(hydroxymethyl) tricyclo[5.2.1.0$^{2,6}$]decane with 2-isocyanatoethyl methacrylate. 2-isocyanatoethyl methacrylate is commercially available or can be synthesized according to the preparation specification from DE 33 38 077 A1 by phosgenation of dihydrooxazines.

The reaction product obtained (Formula (1)) of 2-isocyanatoethyl methacrylate with 3(4), 8(9)-bis(hydroxymethyl) tricyclo[5.2.1.0$^{2,6}$]decane in a formulation following curing has a lower reaction shrinkage and a high mechanical strength.

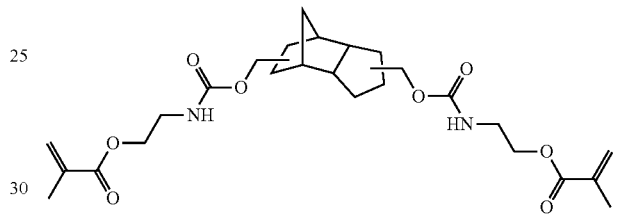

Formula (1)

The urethane of Formula (1) still has two hydrogen atoms capable of reacting with nitrogen, which now in a second reaction stage are further reacted with excess isocyanate to form a compound according to the invention. In the process the allophanate of Formula (2) initially forms as a tetrafunctionalized radically cross-linkable compound. In turn this monomer also still has hydrogen atoms capable of reacting with nitrogen, which according to the invention when reacting with further isocyanate form the hexafunctionalized, radically curable allophanate of Formula (3).

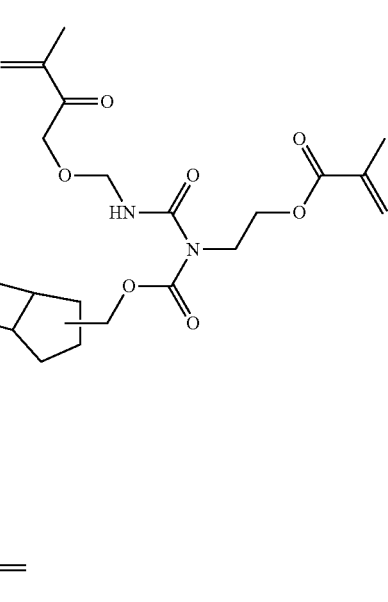

Formula (2)

Formula (3)

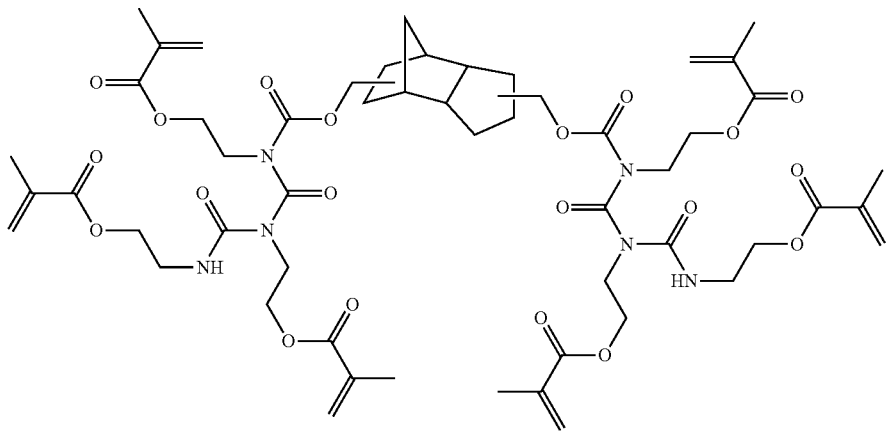

Alternatively the 3(4), 8(9)-bis(hydroxymethyl)tricyclo[5.2.1.0²,⁶]decane can also be brought into a reaction with methacryloyl isocyanate. Methacryloyl isocyanate is commercially available or can be obtained by reacting methacrylamide with oxalyl chloride, as described in EP 0 143 613 B1. Through the reaction of 3(4), 8(9)-bis(hydroxymethyl)tricyclo[5.2.1.0²,⁶]decane with methacryloyl isocyanate a compound of Formula (4) is obtained:

Formula (4)

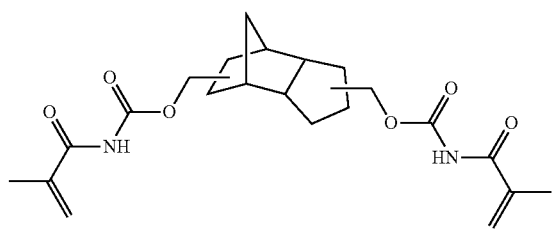

The remaining hydrogen atoms able to react with nitrogen of the compound of Formula (4) can then in turn be reacted in isocyanate reactions to form allophanates. The reaction product with 2-isocyanatoethyl methacrylate (Formula (5)) is shown here as an example.

Formula (5)

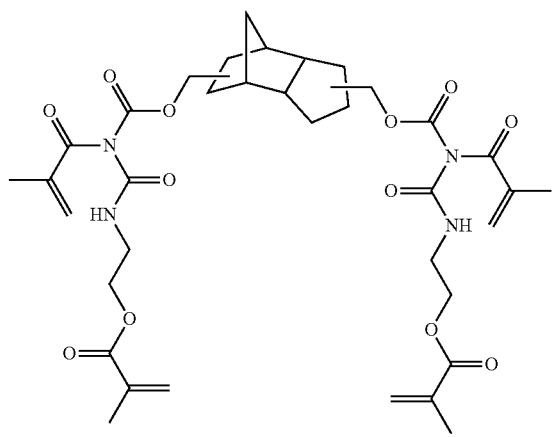

2.) Starting with 3(4), 8(9)-bis(carboxylic acid)tricyclo[5.2.1.0²,⁶]decane

The 3(4), 8(9)-bis(carboxylic acid)tricyclo[5.2.1.0²,⁶]decane is preparable by simple oxidation of the commercially available 3(4), 8(9)-bis(formyl)tricyclo[5.2.1.0²,⁶]decane. Reaction of the dicarboxylic acid with 2-isocyanatoethyl methacrylate produces the amide of Formula (8):

Formula (8)

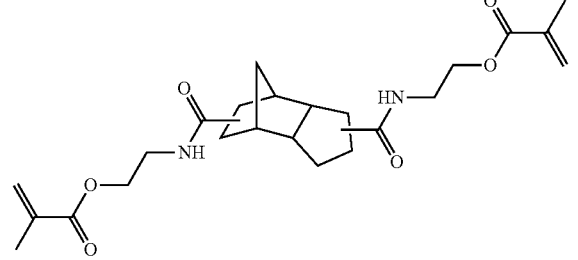

Further reaction of the two amide-hydrogen atoms of the amide of Formula (8) capable of reacting with 2-isocyanatoethyl methacrylate produces the acyl urea of Formula (9).

Formula (9)

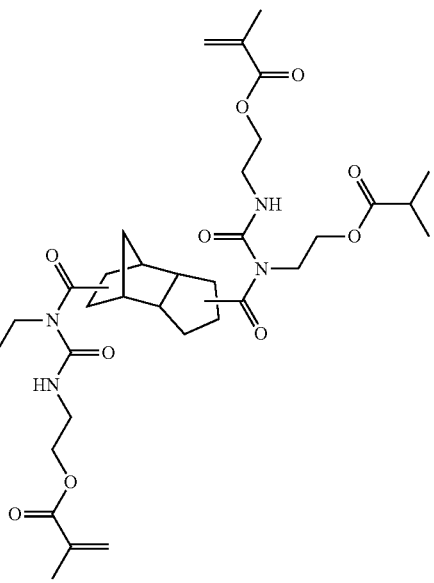

If 3(4), 8(9)-bis(carboxylic acid)tricyclo[5.2.1.0$^{2,6}$]decane is reacted with methacryloyl isocyanate, the imide of Formula (10) results. The hydrogen atoms that react with nitrogen can here also be further reacted in isocyanate reactions.

Formula (10)

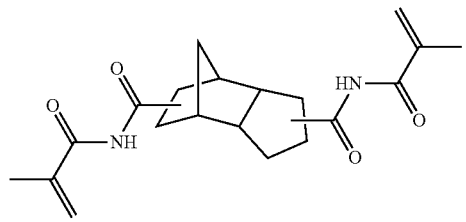

3.) Starting with 3(4), 8(9)-bis(isocyanatomethyl)tricyclo [5.2.1.0$^{2,6}$]decane The 3(4), 8(9)-bis(isocyanatomethyl)tricyclo[5.2.1.0$^{2,6}$] decane is in itself known and is one of the diisocyanate compounds commonly used in industrial applications (see DE 37 03 120 A1 and WO 2009/065873 A2). The conducting according to the invention of the second reaction stage of the isocyanate-alcohol reaction can be initiated not only starting with tricyclodecandiol and the isocyanatoethyl methacrylate, but also starting with the tricyclodecane diisocyanate and hydroxyethyl methacrylate. Through stoichiometric reaction of the two reactants the urethane of Formula (11) is obtained.

Formula (11)

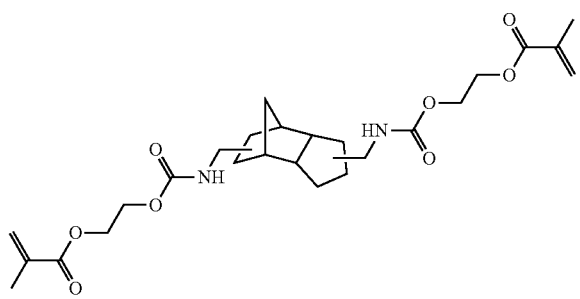

This carbamate (Formula (11)) also has two hydrogen atoms capable of reacting with nitrogen, which can be further reacted with an excess of bis(isocyanatomethyl)tricyclo [5.2.1.0$^{2,6}$]decane to form the diisocyanate of Formula (12).

Formula (12)

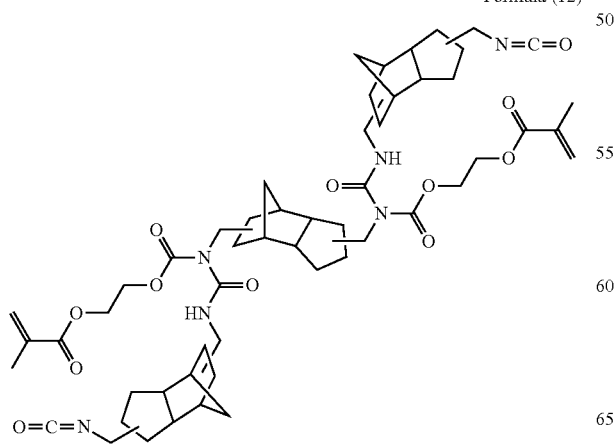

Reaction of the allophanate diisocyanate (Formula 12) with methacrylic acid produces the compound of Formula (13).

Formula (13)

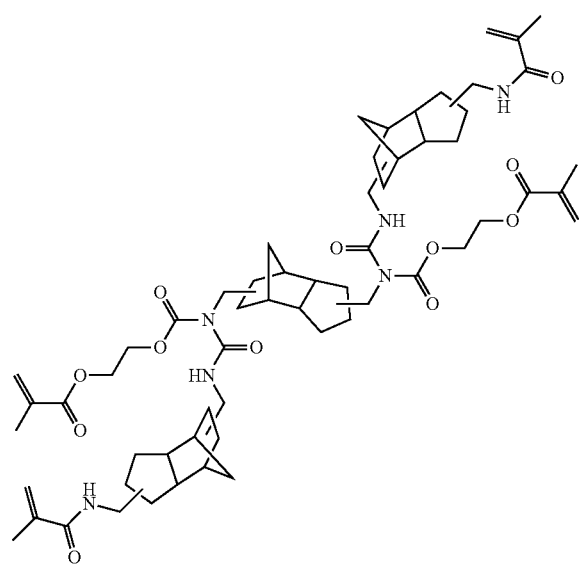

Instead of hydroxyethyl methacrylate in the reactions described by way of example above other hydroxyl compounds of (meth)acrylates can be used, wherein mixtures of acrylates and methacrylates can also be used. So—analogously to the above example—3(4), 8(9)-bis(isocyanatomethyl)tricyclo[5.2.1.0$^{2,6}$]decane can be reacted. Here, preferred hydroxyl compounds of (meth)acrylates are those expressly mentioned above.

These compounds have both (meth)acrylate groups and hydroxy groups. The latter can react with isocyanate groups in the manner described above for the reaction between hydroxyethyl methacrylate and 3(4), 8(9)-bis(isocyanatomethyl)-tricyclo[5.2.1.0$^{2,6}$]decane. Thus in a single reaction step a high degree of functionalization can be achieved.

3(4), 8(9)-bis(isocyanatomethyl)tricyclo[5.2.1.0$^{2,6}$]decane can be reacted with 2-carboxylic acid-methacrylate to form the corresponding amide of Formula (16).

Formula (16)

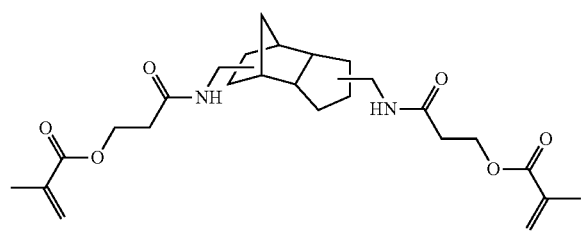

Reacting of the amide of Formula (16) with 2-isocyanatoethyl methacrylate produces the acyl urea of Formula (17).

Formula (17)
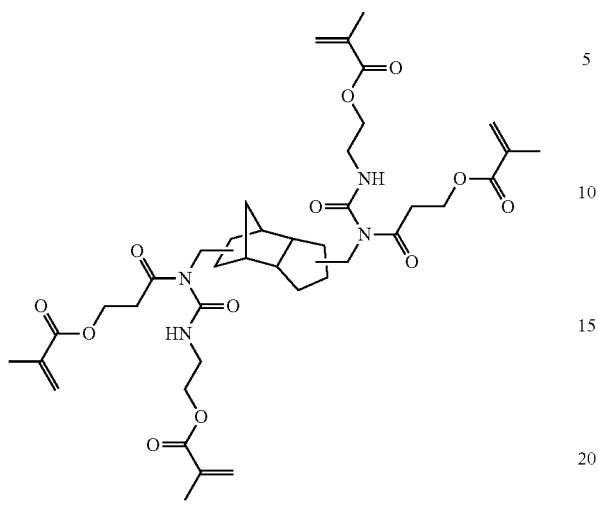
The amide of Formula (16) can also be reacted with an excess of 3(4), 8(9)-bis(isocyanatomethyl)tricyclo[5.2.1.0$^{2,6}$]decane to form the corresponding isocyanate, wherein the isocyanate so formed is further reacted with hydroxyethyl methacrylate to form the cross-linkable monomer of Formula (18).
Formula (18)
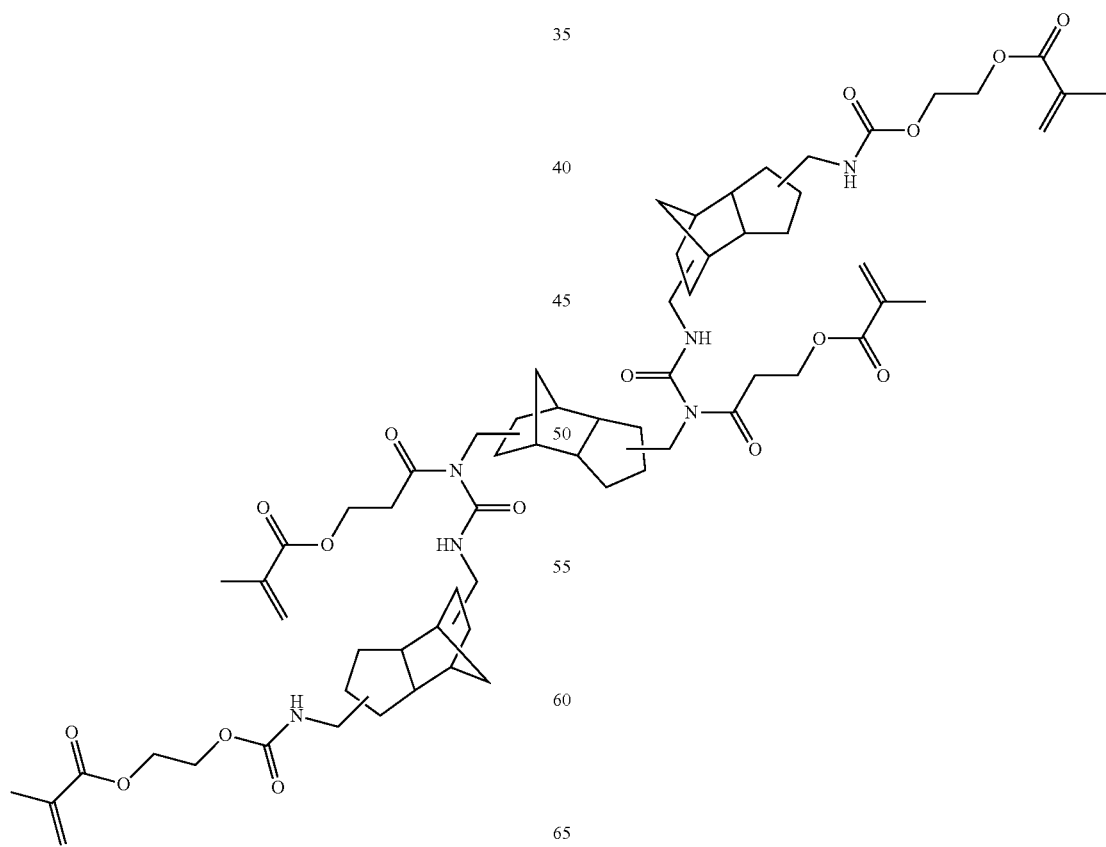

If 3(4), 8(9)-bis(isocyanatomethyl)tricyclo[5.2.1.0²,⁶]decane is reacted with 2-methacryloyloxy ethyl hydrogen succinate, then the amide of Formula (19) is obtained, which is further reacted with 2-isocyanatoethyl methacrylate to form the acyl urea of Formula (20).
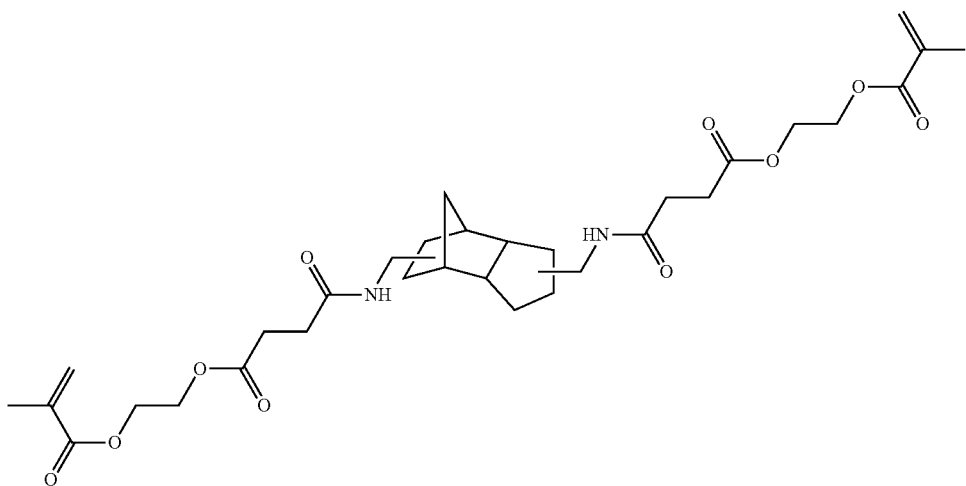
Formula (19)
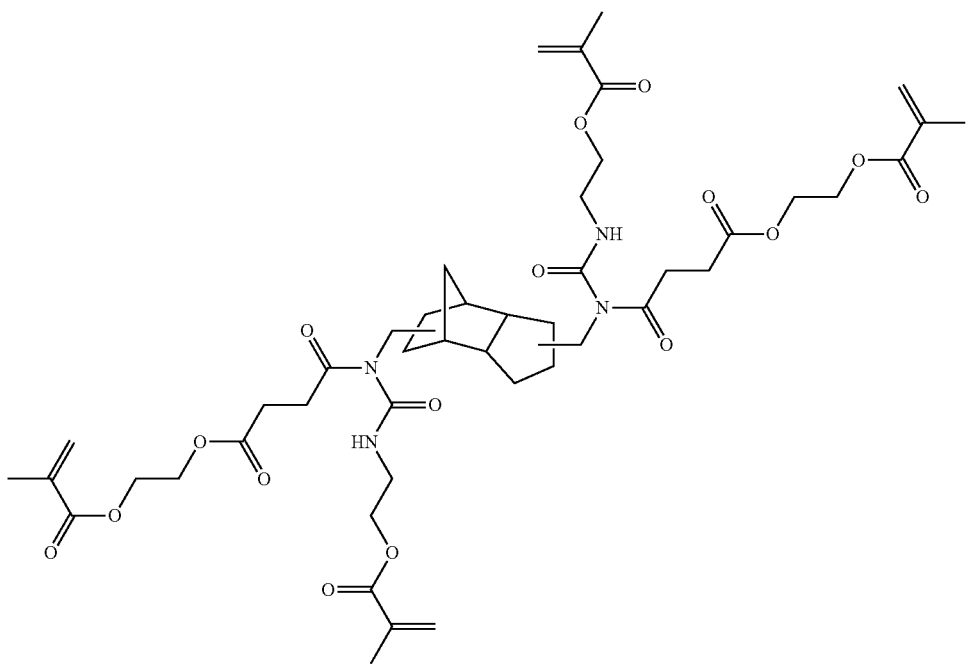
Formula (20)

Further suitable carboxylic acid methacrylates can be obtained from reactions between di- or tetracarboxylic acid mono- or dianhydride with suitable OH-functionalized, curable compounds such as for example 2-hydroxyethyl methacrylate.

4.) Starting with 3(4), 8(9)-bis(aminomethyl)tricyclo[5.2.1.0$^{2,6}$]decane

The 3(4), 8(9)-bis(aminomethyl)tricyclo[5.2.1.0$^{2,6}$]decane is in itself known or can be prepared for example by reaction of the corresponding tosylates with ammonia. Reaction of the 3(4), 8(9)-bis(aminomethyl)tricyclo[5.2.1.0$^{2,6}$]decane with 2-isocyanatoethyl methacrylate results in the urea compound of Formula (26) known from EP 0209700 A2.

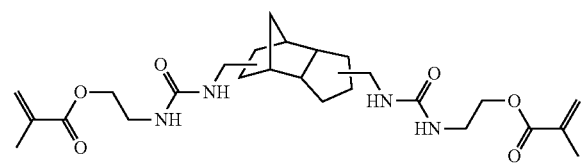

Formula (26)

Here again, there are still active hydrogen atoms capable of reacting with nitrogen which for example with an excess of isocyanate react to form the biuret of Formula (27).

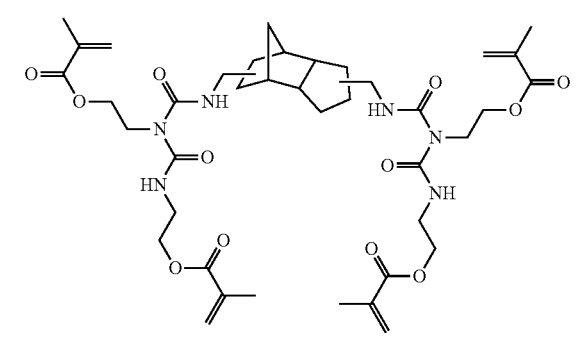

Formula (27)

The 3(4), 8(9)-bis(aminomethyl)tricyclo[5.2.1.0$^{2,6}$]decane can also be brought into a reaction with methacryloyl isocyanate to form the corresponding acyl urea. The further reaction of the remaining hydrogen atoms reactive to nitrogen with methacryloyl isocyanate provides the biuret of Formula (28).

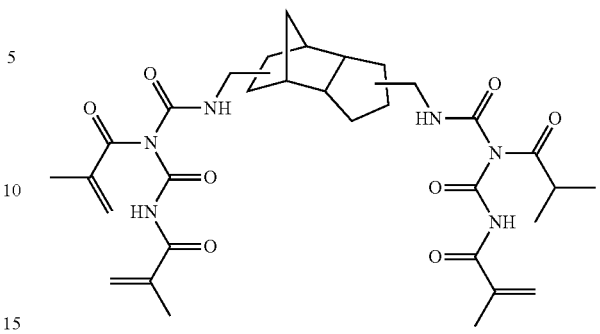

Formula (28)

By analogy to the monomers described above, which comprise a polyalicyclic structure element Q derived from the tricyclo[5.2.1.0$^{2,6}$]decane, monomers can also be prepared, which comprise a polyalicyclic structure element Q derived from a tricyclo[3.3.1.1$^{3,7}$]decane (adamantane). The following reaction products are shown by way of examples:

Formula (29)

The reaction of the compound of Formula (11) with diisocyanatoadamantane [(bis(isocyanatomethyl)tricyclo[3.3.1.1$^{3,7}$]decane] provides a monomer according to the invention, the molecule of which comprises two polyalicylic structure elements that differ from one another, as shown in the following graphic formula of the compound of Formula (69).

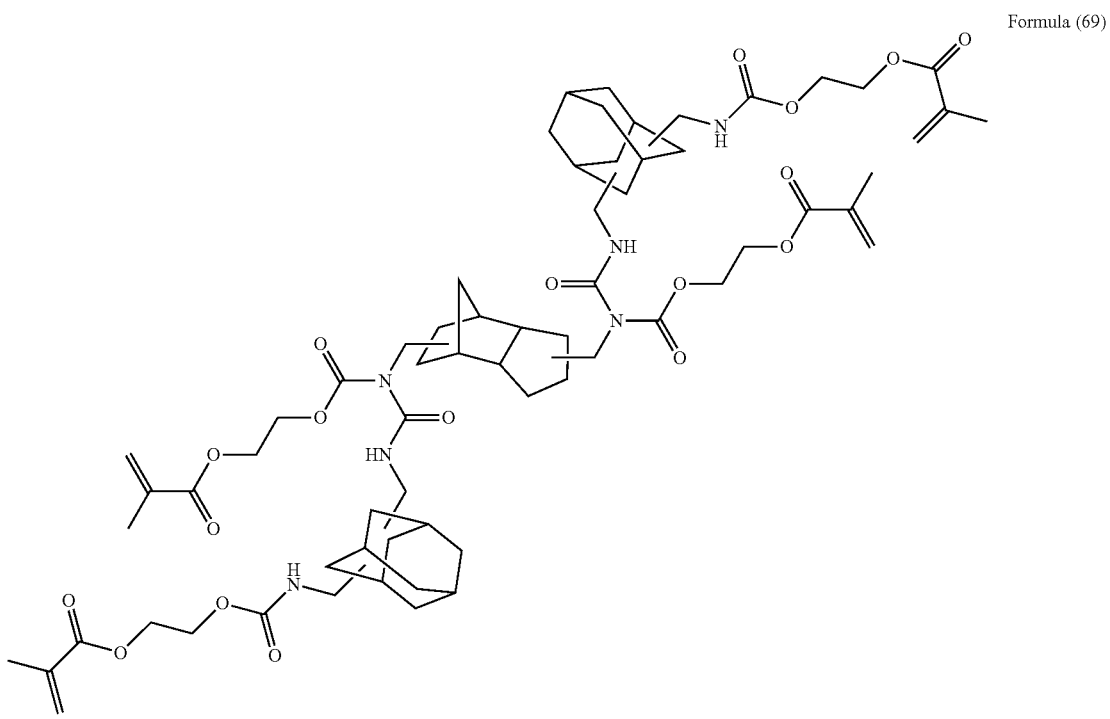

Formula (69)

Component (a2): Monofunctionalized C1-C5-Alkyl Methacrylates

Component (a2) consists of one, two or a plurality of radically polymerizable monofunctionalized monomers from the group consisting of methyl methacrylate, ethyl methacrylate, propyl methacrylate, butyl methacrylate and pentyl methacrylate, Particular preference is for lacquer compositions according to the invention comprising a component (a2), comprising methyl methacrylate or consisting of methyl methacrylate, since then particularly good results in the context of this invention have been achieved.

The total quantity of component (a2) is preferably at least 5 wt. %, preferably at least 8 wt. %, in each case in relation to the total weight of the lacquer composition according to the invention.

The total quantity of component (a2), in particular of methyl methacrylate, is preferably in the range 5 through 45 wt. %, preferably in the range 8 through 40 wt. %, in each case in relation to the total weight of the lacquer composition according to the invention.

Component (a3): Monomers with Three or a Plurality of (Meth)Acrylate Groups

The optional component (a3) consists of one, two or a plurality of radically polymerizable monomers from the group consisting of further radically polymerizable monomers with three, four, five, six or a plurality of (meth)acrylate groups, preferably with three to six acrylate groups.

Preference as component (a3) is for acrylate monomers, since these are significantly faster in polymerization than the corresponding methacrylates, i.e. they allow a fast polymerization process and a faster curing.

Particular preference is for lacquer compositions according to the invention comprising a component (a3), comprising dipentaerythritol pentaacrylate or consisting of dipentaerythritol pentaacrylate, since with this particularly good results in the context of this invention have been achieved.

Preferred lacquer compositions according to the invention therefore contain both methyl methacrylate (component a2) and dipentaerythritol pentaacrylate (component a3).

With such lacquer compositions particularly good results in the context of the present invention have been achieved.

The total quantity of component (a3) is preferably at least 5 wt. %, preferably at least 8 wt. %, in each case in relation to the total weight of the lacquer composition according to the invention.

The total quantity of component (a3), in particular of dipentaerythritol pentaacrylate, is preferably in the range 5 through 65 wt. %, preferably in the range 8 through 60 wt. %, in each case with reference to the total weight of the lacquer composition according to the invention.

Component (a4): Further Radically Polymerizable Monomers from the Group Consisting of Acrylates and Methacrylates, Preferably from the Group of Methacrylates, The optional constituent, that does not count as a component (a1), (a2) and (a3) of the matrix-forming monomer mixture is made up of radically polymerizable monomers selected from the group consisting of acrylates and methacrylates.

The radically polymerizable monomers of component (a4) preferably have at least two ethylenic groups.

In the patent literature a number of diacrylate and dimethacrylate monomers are mentioned (for example also in DE 3941629 A1, which by way of reference is a constituent of this application, in particular the disclosure between column 6, line 15 and column 8, line 10), which are suitable for use in a lacquer composition according to the invention.

Lacquer compositions according to the invention can also contain as component (a4) one or a plurality of dimethacrylate monomers, preferably selected from the group consisting of ethylene glycol dimethacrylate (EGDMA), 1,6-hexandiol dimethacrylate (HEDMA), triethylene glycol dimethacrylate (TEDMA), 1,12-dodecandiol dimethacrylate (DODMA), ethoxylated bisphenol A dimethacrylate, polyethylene glycol dimethacrylate (PEGDMA), 7,7,9-trimethyl-4,13-dioxo-5,12-diazahexadecan-1,16-dioxydimethacrylate (UDMA), butane diol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, and glycerin dimethacrylate.

While bisphenol-A-glycidyl-methacrylate (Bis-GMA) can indeed be used, preferably a lacquer composition according to the invention, in particular a dental lacquer composition according to the invention, does not contain the compound Bis-GMA, however. Preferably a lacquer composition according to the invention, in particular a dental lacquer composition according to the invention, is free from all compounds with a bisphenol-A structure element.

The racially polymerizable monomers of component (a4) which are thus not part of component (a1) can also be hydroxyl compounds. Here all hydroxyl compounds of acrylates and methacrylates normally used in dental chemistry can be used. Preference is for hydroxyl compounds of methacrylates, and here in turn preference is for 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol dimethacrylate, glycerin dimethacrylate, and 2,2-bis[4-[3-methacryloyloxy-2-hydroxypropoxy]phenyl]propane.

As a further constituent photocurable acrylate or methacrylate monomers based on polysiloxanes, as for example described in DE 19903177 or in DE 4416857, which by way of reference are a constituent of this application, can also be used.

A lacquer composition according to the invention, in particular a dental lacquer composition according to the invention, can further in component (a4) contain one or a plurality of acid group-containing acrylate and/or methacrylate monomers. Such acid group-containing monomers can preferably have a carboxylic acid, a phosphoric acid, a phosphonic acid, a sulfonic acid and/or a thiophosphoric acid function. The monomer can contain one or a large number of acid functions in a molecule.

Suitable monomers containing a phosphoric acid group are, for example, 2-(meth)acryloyloxyethyl dihydrogen phosphate, bis[2-(meth)acryloyloxyethyl]hydrogen phosphate, 2-(meth)acryloyloxyethylphenyl hydrogen phosphate, 6-(meth)-acryloyloxyhexyl dihydrogen phosphate, 10-(meth)acryloyloxydecyl dihydrogen phosphate (MDP), 6-(meth)-acryloyloxyhexylphenyl hydrogen phosphate, 10-(meth)acryloyloxydecyl dihydrogen phosphate, 1,3-di-(meth)acryloyloxypropane-2-dihydrogen phosphate, 1,3-di-(meth)acryloyloxypropane-2-phenyl hydrogen phosphate and bis[5-(2-(meth)acryloyloxyethoxycarbonyl)heptyl]hydrogen phosphate.

Suitable monomers containing a carboxylic acid group are for example, 4-(meth)acryloxyethyl trimellith acid (4-MET), 4-(meth)acryloxyethyl trimellith acid anhydride (4-META), 4-(meth)acryloxydecyl trimellith acid, 4-(meth)acryloxydecyl trimellith acid anhydride, 11-(meth)acryloyloxy-1,1-undecane dicarboxylic acid, 1,4-di(meth)acryloyloxy pyromellith acid, 2-(meth)acryloyloxyethyl maleic acid, 2-(meth)acryloyloxyethyl phthalic acid and 2-(meth)acryloyloxyethyl hexahydrophthalic acid.

Further suitable acid group-containing monomers are mentioned in, for example, EP 0980682 A1 (in particular paragraphs [0059]-[0065]) or EP 0948955 A1 (in particular paragraphs [0031]-[0034]), which by way of reference are a constituent of this application.

Furthermore, phosphoric acid esters with glycerin dimethacrylate or with hydroxyethylmethacrylate or with hydroxypropylmethacrylate can also be used.

The monomers mentioned can be used individually or in mixtures.

Constituent (b): Initiators and/or Catalysts

A lacquer composition according to the invention is preferably photocurable and/or chemically curable. Preference is for a lacquer composition according to the invention, wherein constituent (b) comprises or consists of one or a plurality of photocuring initiators and/or one or a plurality of initiators for chemical curing.

The total quantity of component (b), in particular of phosphine oxide inhibitors, is preferably in the range 1 through 6 wt. %, preferably in the range 1.5 through 5 wt. %, in each case with reference to the total weight of the lacquer composition according to the invention.

Preferred lacquer compositions according to the invention are photocurable and comprise photocuring initiators. Examples of a photoinitiator include substances which have solely a photo-sensitizing effect and combinations of sensitizers and accelerators.

Examples of photosensitizers are alpha-diketones, benzoin alkyl ethers, thioxanthones, benzophenones, acylphosphinoxides, acetophenones, ketals, titanocenes, sensitizing colorants, etc. The sensitizers can be used alone or in combination. Specific substance examples of the various classes can be found, for example, in DE 10 2006 019 092 A1 or in DE 39 41 629 C2, which by way of reference are a constituent of this application.

Examples of accelerators, which are used together with the sensitizers, are tertiary amines, secondary amines, barbituric acids, tin compounds, aldehydes and sulfur compounds. Specific substance examples of the various classes can be found in DE 10 2006 019 092 or in DE 39 41 629 C2, which by way of reference are a constituent of this application.

Further suitable initiators and initiator combinations are described in DE 601 16 142, which by way of reference are a constituent of this application.

The photoinitiators that can be used in connection with the present invention are characterized in that through the absorption of light in the wavelength range 300 nm through 700 nm, preferably 350 nm through 600 nm and particularly preferably 380 through 500 nm, optionally in combination with one or a plurality of co-initiators, they can bring about the curing of a lacquer composition according to the invention, in particular a dental lacquer composition according to the invention.

The absorption maximum of campherquinone (CQ) is approximately 470 nm and thus in the range of blue light. Campherquinone (CQ) is one of the $PI_2$-initiators and is regularly used together with a co-initiator.

A lacquer composition according to the invention preferably contains a combination of an alpha-diketone and an aromatic tertiary amine, preferably the combination is of campherquinone (CQ) and ethyl-p-N,N-dimethylaminobenzoate (DABE)

Particularly preferred initiators as component (b) of a lacquer composition according to the invention are phosphine oxide, in particular acyl phosphine oxide.

With these phosphine oxide initiators lacquer compositions according to the invention can be obtained which cure without smear layers. Further preferred phosphine oxides are phenyl-bis(2,4,6-trimethylbenzoyl)phosphine oxide and/or 2,4,6-trimethylbenzoyldiphenyl phosphine oxide.

Likewise preferred is the further combination of the "alpha-diketone/aromatic tertiary amine" system with a phosphine oxide, in particular with phenyl-bis(2,4,6-trimethylbenzoyl)phosphine oxide and/or 2,4,6-trimethylbenzoyl-diphenyl phosphine oxide.

Regarding the structures of suitable phosphine oxides for use in a lacquer composition according to the invention reference is made to printed publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. Nos. 7,148,382 B2, 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which by way of reference are a constituent of this application.

The phosphine oxides indicated in these printed publications are particularly suitable on their own or in combination with the "alpha-diketone/amine" system as a photopolymerization initiator system in a lacquer composition according to the invention.

Alternatively borate salts, as described for example in U.S. Pat. Nos. 4,772,530, 4,954,414, 4,874,450, 5,055,372 and 5,057,393, can be used as photoinitiators, which by way of reference are a constituent of this application.

Further suitable photoinitiators are described in J.-P. Fouassier, Photoinitiation, Photopolymerization and Photocuring, Hanser Publishers, Munich, Vienna, New York 1995 and in J. F. Rabek (publisher), Radiation Curing in Polymer Science and Technology, Vol. II, Elsevier Applied Science, London, N.Y. 1993, which by way of reference are a constituent of this application.

Various initiators for a chemical curing will be known to a person skilled in the art. In this connection reference is made by way of example to EP 1 720 506.

Preferred initiators for chemical curing are benzoyl peroxide, lauroyl peroxide in particular dibenzoyl peroxide in combination with amines such as N,N-dimethyl-p-toluidine, N,N-dihydroxyethyl-p-toluidine and structurally related amines.

Here the peroxides and the amines are spread across two different components of the dental material. During the mixing of the amine-containing components (so-called base paste) with the peroxide-containing components (so-called initiator or catalyst paste) through the reaction of amine and peroxide (redox reaction) the radical reaction is initiated.

Dual-curing systems comprise a combination of photoinitiators and initiators for chemical curing.

By way of example, the base paste can also contain a photoinitiator, so that the base paste can be used either on its own as a photo-curing agent or together with the initiator paste as a photo- and self-curing dental material.

Apart from the organic peroxide compounds with an oxidative effect, barbituric acids or barbituric acid derivatives and malonyl sulfamides can also be used as redox systems.

Of the barbituric acid systems the so-called Bredereck systems are of great significance. Examples of suitable Bredereck systems and references to the corresponding patent literature can be found in EP 1 839 640 and in DE 14 95 520, WO 02/092021 or in WO 02/092023, which by way of reference are a constituent of this application.

Suitable malonyl sulfamides are described in EP 0 059 451 which by way of reference is a constituent of this application. Preferred compounds here are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2.6, 6-diocytyl-4-isobutylmalonyl sulfamide.

Sulfur compounds in the oxidation stage +2 or +4 such as sodium benzene sulfinate or sodium paratoluene sulfinate can also be used.

In order to accelerate the curing the polymerization can be carried out in the presence of compounds of heavy metals such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethyl hexanoate, copper di(methacrylate) and copper napththenate.

Constituent (c): Filler Component

A lacquer composition according to the invention can contain an amount of the filler component (c) of 0 through 60 wt. %, in relation to the total weight of the lacquer composition according to the invention, wherein the filler component comprises one, two or a plurality of fillers.

According to the statements above and below the present invention also relates to a lacquer composition (as defined above) comprising (c) 0 through 60 wt. % of a filler component, comprising one, two or a plurality of fillers selected from the group consisting of
- (c1) a total quantity in the range 0 through 60 wt. % of non-agglomerated, preferably surface-modified, nanoparticles with an average particle size of less than 200 nm (preferably less than 100 nm, particularly preferably less than 60 nm),
- (c2) a total quantity in the range of 0 through 10 wt. % of microparticles with an average particle size in the range 0.4 µm through 10 µm, and
- (c3) a total quantity in the range 0 through 15 wt. % of further fillers, preferably 0 through 10 wt. %, preferably 0 through 5 wt. %, of further fillers, wherein the weight percentages given in each case relate to the total weight of the lacquer composition.

The average particle size $d_{50}$ of the filler particles to be used optionally according to the invention of the filler component (c) of a lacquer composition according to the invention is determined by means of light scattering (laser diffraction), preferably with a Beckman Coulter LS13320 particle size analyzer.

Filler component (c) can preferably comprise a filler (c1) in the form of non-agglomerated nanoparticles with an average particle size of less than 200 nm.

Filler component (c) can preferably comprise a filler (c1) in the form of non-agglomerated, organically surface-modified nanoparticles with an average particle size of less than 200 nm.

Filler component (c) can preferably alternatively or additionally comprise a filler (c2) in the form of microparticles with an average particle size in the range 0.4 µm through 10 µm.

Filler component (c) comprises in a preferred configuration a mixture of a first filler (c1) in the form of non-agglomerated, organically surface-modified nanoparticles with an average particle size of less than 200 nm and a second filler (c2) in the form of microparticles with an average particle size in the range 0.4 µm through 10 µm.

Through the combination of (c1) nanoparticles and (c2) microparticles in a preferred lacquer composition according to the invention complete and even volumetric filling of the lacquer composition is achieved. In this way both the shrinkage of the lacquer composition as the polymer matrix cures and the sensitivity of the lacquer composition to abrasion are reduced.

In particular for the setting of the rheology a lacquer composition according to the invention preferably comprises a low quantity of pyrogenic silica, preferably in a quantity in the range 0.1 through 5 wt. %, more preferably in the range 0.5 through 2.5 wt. %, in relation to the total weight of the lacquer composition.

Component (c1): Non-agglomerated Nanoparticles

In connection with the present invention, nanoparticles mean particles with an average particle size of less than 200 nm. Preferably the average particle size is less than 100 nm and particularly preferably less than 60 nm.

The filler component (c) of a lacquer composition according to the invention can comprise a filler (c1) in a quantity of 0 through 60 wt. %, in relation to the total weight of the lacquer composition.

The amount of non-agglomerated, optional organically surface-modified nanoparticles with an average particle size of less than 200 nm here should be not more than 60 wt. %, since the processability of the lacquer composition is then no longer sufficient: because of the high solid content they may then become too viscous.

The materials for the nanoparticles to be used according to the invention are preferably oxides or mixed oxides and preferably selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof. Here, as explained, the preferred oxidic nanoparticles are not agglomerated.

In a preferred configuration the nanoscale particles are present in non-agglomerated form, for example dispersed in a medium, preferably in monodisperse form.

In order to allow the nanoparticles to bond properly in the polymer matrix of a lacquer composition according to the invention, the surfaces of the nanoparticles (preferably the preferred oxidic nanoparticles) are organically modified, i.e. their surfaces have organic structure elements. An example of surface treatment of the fillers is the use of a silane. Methacryloxypropyltrimethoxysilane is particularly well-suited as a bonding agent.

If for the filler component (c) exclusively a nanoscale filler (c1) is used, then transparent sealing materials can be obtained (see WO 01/30307 A1 and WO 2007/028159 A2). Very good abrasion properties are then achieved.

The transparent dental lacquer compositions according to the invention, compared to the products from the prior art, are also characterized by a highly improved surface affinity (in the uncured state) to the tooth enamel, in particular the dry tooth enamel, and by much lower water absorption (in the cured state).

Therefore in a preferred embodiment the filler component (c) of a lacquer composition according to the invention comprises exclusively (c1) non-agglomerated nanoparticles with an average particle size of less than 200 nm.

In a further preferred embodiment the filler component (c) of a lacquer composition according to the invention consists of exclusively (c1) non-agglomerated, organically surface-modified nanoparticles with an average particle size of less than 200 nm.

Component (c2): Microparticles with an Average Particle Size in the Range 0.4 μm through 10 μm In connection with the present invention, microparticles mean particles with an average particle size of 400 nm through 10 μm. Preferably, the average particle size is less than 5 μm. Our own research has shown that the volumetric filling of the lacquer composition that can already be achieved with the microparticles is more complete and even the smaller the microparticles are.

The filler component (c) of a lacquer composition according to the invention can comprise a filler (c2) in a quantity of 0 through 10 wt. %, in relation to the total weight of the lacquer composition.

The microparticles of component (c2) can have a monomodal or polymodal, for example a bimodal, particle size distribution. Microparticles with a bimodal or multimodal particle size distribution are preferred according to the invention, since with these a more complete volumetric filling can be achieved than with the general use of microparticles with monomodal particle size distribution. In the case of a bi- or multimodal particle size distribution the particles from the fractions with the larger particle sizes bring about a coarse filling of the volume, while the particles from the fraction with the smaller particle sizes where possible fill the cavities between the particles from the fractions with the larger particle sizes.

Preferably, therefore, in a lacquer composition according to the invention a component (c2) will be used which contains two or a plurality of fractions of microparticles wherein the average particle sizes of the fractions differ from one another.

Preferably component (c2) contains at least two microparticle fractions, wherein the average particle sizes of these differ from one another by at least 1 μm.

The microparticles of various fractions can consist of the same or different materials; here a plurality of fractions of microparticles can be present, the average particle sizes of which are approximately the same or are within a certain range, wherein the particle materials differ between the fractions.

A lacquer composition according to the invention preferably comprises a component (c2), having one or a plurality of first microparticle fractions, which in each case have an average particle size in the range 1 μm through 10 μm, preferably 1 μm through 5 μm, and one or a plurality of second microparticle fractions, which in each case have an average particle size in the range >0.4 μm to <1 μm (e.g. larger than 0.4 μm, but smaller than 1 μm), preferably 0.5 μm through 0.8 μm.

The ratio of the total weight of the first microparticle fractions to the total weight of the second microparticle fractions is preferably in the range 1:1 through 10:1, preferably in the range 1.5:1 through 5:1.

The ratio of the average grain size of the or a first microparticle fraction to the average grain size of the or a second microparticle fraction of component (c2) is preferably in the range 1.5:1 through 10:1, preferably in the range 2:1 through 5:1.

In an particularly preferred lacquer composition according to the invention the component (c2) comprises one or a plurality of first microparticle fractions, which in each case have an average particle size in the range 1 μm through 10 μm, preferably 1 μm through 5 μm, and one or a plurality of second microparticle fractions, which in each case have an average particle size in the range >0.4 μm through <1 μm, preferably 0.5 μm through 0.8 μm, wherein the ratio of the total weight of the first microparticle fractions to the total weight of the second microparticle fractions is in the range 1:1 through 10:1, preferably 1.5:1 through 5:1 and/or the ratio of the average grain size of the or a first microparticle fraction to the average grain size of the or a second microparticle fraction of component (c2) is in the range 1.5:1 through 10:1, preferably 2:1 through 5:1.

The base materials for the microparticles to be used according to the invention in surface-modified form are preferably selected from the group consisting of amorphous materials with a $SiO_2$, $ZrO_2$ and/or $TiO_2$ base, as well as mixed oxides, pyrogenic silica or precipitated silica, such as quartz glass ceramic or glass powder (in particular dental glass powder), barium or strontium glasses, fluoride ion-emitting glasses, oxides of aluminum or silicon, zeolites, apatites, zirconium silicates, hardly soluble metal salts such as barium sulfate or calcium fluoride and radiopaque fillers such as ytterbium fluoride.

For improved bonding in the polymer matrix of a lacquer composition according to the invention the microparticles are preferably organically surface-modified. One example of surface treatment of the fillers is the use of a silane, leading to silanized microparticles. Methacryloxypropyltrimethoxysilane is particularly well-suited for surface treatment (as a bonding agent).

In an particularly preferred lacquer composition according to the invention at least part of the microparticles of component (c2) is made up of organically surface-modified particles, preferably silanized particles and/or at least part of the microparticles of component (c2) is made up of dental glass particles; preferably at least part of the microparticles of component (c2) is organically surface-modified dental glass particles, preferably silanized dental glass particles.

Preferably in these cases component (c2) is characterized by a bi- or multi-modal particle size distribution, in particular a bi- or multi-modal particle size distribution with the preferred features described above.

Component (c3)—Further Fillers

The filler component (c) of a lacquer composition according to the invention can further comprise a filler (c3) in a quantity of 0 through 15 wt. %, preferably in a quantity of 0 through 10 wt. %, preferably in a quantity of 0 through 5 wt. %, preferably in a quantity of 0 through 2.5 wt. %, in each case in relation to the total weight of the lacquer composition.

The quantity ranges indicated above apply in particular for many fillers with agglomerated particles, since such fillers can lead to an undesired high viscosity of the lacquer compositions, so that the lacquer composition is significantly less, or even no longer, suitable for the stated intended use.

Thus, for example, filler materials with a strengthening effect such as glass fibers, polyamide or carbon fibers can be used. A lacquer composition according to the invention can also contain fine particle splinters or bead polymers, wherein the bead polymers can be homo- or copolymers of organically curable monomers.

Constituent (d): Optional Further Additives

A lacquer composition according to the invention in some cases comprises one or a plurality of further additives.

These additives can have various functions. Normal additives for use in dental lacquer compositions are known to a person skilled in the art who will select the appropriate additive(s) according to the desired function. In the following examples of typical additives and their functions are provided.

Photocurable dental lacquer compositions, as preferred according to the invention, preferably contain one or a plurality of inhibitors, also referred to as stabilizers. These are normally added in order to prevent spontaneous polymerization. They react with prematurely forming radicals, which are intercepted, prevent premature polymerization and increase the storage stability of the photocurable dental composition. Common inhibitors are phenol derivates such as hydroquinone monomethylether (HQME) or 2,6-di-tert.butyl-4-methylphenol (BHT). Further inhibitors such as tert.-butyl-hydroxy anisol (BHA), 2,2 diphenyl-1-picrylhydrazyl, galvinoxyl, triphenylmethyl radicals, 2,3,6,6,-tetramethylpiperidinyl-1-oxyl radicals (TEMPO) and derivatives of TEMPO or phenothiazine and derivatives of this compound are described in EP 0 783 880 B1 which by way of reference are a constituent of this application. Alternative inhibitors are indicated in DE 101 19 831 A1 or in EP 1 563 821 A1, which by way of reference are a constituent of this application.

A dental lacquer composition preferred according to the invention thus comprises as an additive one or a plurality of polymerization inhibitors to increase the storage stability of the lacquer composition, preferably selected from the group consisting of hydroquinone monomethylether (HQME), phenols, here preferably 2,6-di-tert.butyl-4-methyl phenol (BHT) and tert.-butylhydroxy anisol (BHA), 2,2-diphenyl-1-picrylhydrazyl radicals, galvinoxyl radicals, triphenylmethyl radicals, 2,3,6,6,-tetramethylpiperidinyl-1-oxyl radicals (TEMPO) and derivatives thereof and phenothiazine and derivatives thereof.

A dental lacquer composition preferred according to the invention comprises as an additive one or a plurality of fluoride-releasing substances, here preferably sodium fluoride and/or aminofluoride.

Additionally, one or a plurality of (preferably dental) surfactants can be a constituent of a lacquer composition according to the invention.

UV absorbers, which for example as a result of their conjugated double bonding systems and aromatic rings are capable of absorbing UV radiation, are in many cases a constituent of a lacquer composition (preferably dental) according to the invention. Examples of UV absorbers are 2-hydroxy-4-methoxybenzophenone, salicylic acid phenyl ester, 3-(2'-hydroxy-5'-methylphenyl)-benzotriazole, or diethyl-2,5-dihydroxy-terephthalate.

Since the teeth are to be rebuilt to look as true to life as possible, it is necessary for the dental lacquer compositions according to the invention to be provided in the most varied of color tones. To this end as a rule inorganic colorants and organic pigments in very small quantities are used, which in preferred configurations are thus used as an additive.

Further optional additives are aromatic substances.

The invention also relates to a method for preparation of a lacquer composition according to the invention, in particular a dental lacquer composition according to the invention, with the following step:
  mixing of constituents (a) and (b), and optionally (c) and optionally (d).

EXAMPLES

The invention is further explained using the following examples. Unless otherwise indicated all data relate to the weight. The following abbreviations are used here:

TCD monomer=bis(methacrylolyoxymethyl)tricyclo[$5.2.1.0^{2,6}$]decane
BHT=2,6-di-tert.butyl-4-methyl phenol (stabilizer)
Nano-$SiO_2$: nanoscale silica was used with an average particle size of 50 nm
Aerosil: Aerosil A200 (Evonik)
Surfactant: BYK307 (Byk-Chemie GmbH)
CA=contact angle with dry tooth enamel Preparation of the Lacquer Compositions Lacquer compositions according to the invention and a lacquer composition not according to the invention were in each case prepared as follows:

The monomers, and initiators and additives are initially homogenized in a plastic container using a KPG stirrer. Then optionally the fillers are added and mixed with a dual-planet mixer.

Measurement Methods:

Flexural strength: 3-point Flexural Strength

The determination of the flexural strength took place in accordance with ISO 4049. In a PTFE mould test specimens were prepared with dimensions of 2×2×50 mm. These were then polymerized for 60 minutes in a light box. After removal from the mold the test specimens were stored for 24 hours at 37° C. in distilled water before being measured. The measurement of the flexural strength took place using a universal testing machine at a traverse speed of 0.75 mm/min and a clamping length of 25 mm until rupture.

Modulus of Elasticity:

The modulus of elasticity was determined from flexural strength measurements by calculating the slope in the linear area.

Water Absorption:

The water absorption was determined analogous to ISO 4049. For this purpose the material to be investigated was filled free from air bubbles in suitable Teflon moulds, and then covered with films and glass plates and the excesses pressed out by means of a screw clamp. The test specimens with a diameter of 15.0±0.1 mm and a height of 1.0±0.1 mm were photocured in segments. Then the test specimens were stored in a desiccator at 37° C. After 22 hours the test specimens were removed, placed in a second desiccator at 23° C. for 2 hours and then weighed to an accuracy of 0.1 mg. This cycle was repeated until a constant weight $m_1$, had been achieved.

Following complete drying two measurements of the diameter were taken at right angles to each other with a measuring accuracy of 0.01 mm and from these the average diameter was calculated. The thickness of the test specimen was measured at the centre and at four evenly spaced points on the circumference to an accuracy of 0.01 mm. The average diameter and the average thickness were used to calculate the volume V.

Then the test specimens were stored for 7 days in water at 37° C., after which they were removed, rinsed with water and dabbed off until no further moisture could be seen on the surface. The test specimens were waved back and forth for 15 seconds in the air and 1 minute after removal from the water they were weighed. The weight is given as $m_2$.

Then the test specimens were again stored in a desiccator at 37° C. After 22 hours the test specimens were removed, placed in a second desiccator at 23° C. for 2 hours and then weighed to an accuracy of 0.1 mg. This cycle was repeated until a constant weight $m_3$, had been achieved.

The water absorption, $W_{sp}$, was calculated according to the following equation:

$$W_{sp} = \frac{m_2 - m_3}{V}$$

Where:

$m_2$ is the weight of the test specimen following storage in water for 7 days in µg;
$m_3$ is the weight of the re-dried test specimen in µg;
V is the volume of the test specimen in mm³.

Surface Affinity: Contact Angle with Dry Tooth Enamel

The surface affinity was determined by measuring the contact angle with the dry tooth enamel.

For the contact angle measurements on dry tooth enamel an extracted human molar was used. Prior to measurement this was dried by wiping with a tissue. Then a drop of the material to be investigated was applied to the enamel area of the tooth. The contact angle was then measured over a period of 30 seconds with a contact angle measuring instrument (DSA 100 from Krüss).

The compositions of the mixtures (in parts by weight) and the results of the measurements are listed in the Tables below.

TABLE 1

| | Example No | | | |
|---|---|---|---|---|
| | 1 | 2 | 3 | Comparison |
| Phosphine oxide initiator | 3.970 | 3.970 | 3.970 | 4.130 |
| UV stabilizer | 0.029 | 0.029 | 0.029 | 0.029 |
| BHT | 0.016 | 0.016 | 0.016 | 0.017 |
| Aerosil | 0.760 | 0.760 | 0.760 | 0.840 |
| Surfactant | 0.760 | 0.760 | 0.760 | 0.840 |
| Methyl methacrylate | 20.14 | 20.16 | 35.13 | 30.51 |
| Dipentaerythritol pentaacrylate | 44.32 | 59.30 | 44.33 | 63.63 |
| TCD monomer | 30.00 | 15.00 | 15.00 | 0.00 |
| Nano-SiO$_2$ | 0.00 | 0.00 | 0.00 | 0.00 |
| Flexural strength [MPa] | 85 | 65 | 94 | 54 |
| Modulus of elasticity [MPa] | 2846 | 2730 | 2656 | 2300 |
| Contact angle [°] dry tooth enamel | 31.9 | 30.2 | 19.8 | 30.8 |
| Water absorption [µg/mm³] | 34.80 | 39.64 | 42.19 | 49.12 |

TABLE 2

| | Example No | | | |
|---|---|---|---|---|
| | 4 | 5 | 6 | 7 |
| Phosphine oxide initiator | 3.970 | 3.970 | 1.998 | 1.998 |
| UV stabilizer | 0.030 | 0.030 | 0.029 | 0.029 |
| BHT | 0.017 | 0.017 | 0.017 | 0.017 |
| Aerosil | 0.764 | 0.764 | 0.000 | 0.000 |
| Surfactant | 0.764 | 0.769 | 0.000 | 0.000 |
| Methyl methacrylate | 42.30 | 20.00 | 9.52 | 9.52 |
| Dipentaerythritol pentaacrylate | 0.00 | 0.00 | 9.52 | 9.52 |
| TCD monomer | 52.15 | 74.45 | 19.05 | 0.00 |
| Monomer of Formula (2) | 0.00 | 0.00 | 0.00 | 19.05 |
| Nano-SiO$_2$ | 0.00 | 0.00 | 59.87 | 59.87 |
| Flexural strength [MPa] | 86 | 70 | 109 | 112 |
| Modulus of elasticity [MPa] | 2917 | 3178 | 3670 | 3735 |
| Contact angle [°] dry tooth enamel | | | 27.4 | 25.6 |
| Water absorption [µg/mm³] | | | 35.13 | 32.17 |

Synthesis of the Compound of Formula (2)

0.95 g (4.84 mmol) of 3(4), 8(9)-bis(hydroxymethyl)tricyclo[5.2.1.0$^{2,6}$]decane were dissolved in 10 ml of toluene and 0.04 g of BHT and 0.103 g of the catalyst solution (0.50 g dibutyltin(II)dilaurate dissolved in 9.50 g toluene) were added. Under agitation 3.00 g (19.34 mmol, 4 equivalents) of isocyanatoethyl methacrylate dissolved in 10 ml of toluene were droppered in. Once addition was complete the dropping funnel was replaced by a reflux condenser and the reaction mixture heated to 120° C. with the continuation of the reaction being monitored by IR spectroscopy. After 72 hours a further 0.102 g of catalyst solution was added and heating continued until no further isocyanate bands were detected. The solvent was removed using the rotary evaporator. The allophanate of formula (2) was obtained in a yield of 3.83 g (4.69 mmol, 97%) as a light yellowy oil.

Examples 1-6 were repeated exchanging the respective TCD monomers used there for the compound of formula (2); these further examples are referred to as Examples S1-S6. All parameters determined in Examples 1-6 were also determined for Examples S1-S6. The values of the parameters determined for Examples S1-S6 are similar to those from Examples 1-6 and to some extent surpass these. This shows in addition to Example 7, that the compound of Formula (2), which is representative of the compounds according to the invention, is eminently suitable for use in composite materials according to the invention.

The invention claimed is:

1. A lacquer composition comprising:
   (a) 35 through 99 wt. %, in relation to the total weight of the lacquer composition, of a monomer component comprising
   (a1) one, two or a plurality of monomers selected from the group consisting of compounds (monomers) with the structure $Q(Y_xZ_e)_b$, wherein the following applies:
   Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups, alkoxy groups, halogen atoms or trifluormethyi groups,
   b is an integer selected from the group of integers 1, 2, 3 and 4,
   each Z represents a structure element, Which independently of any further structure elements Z is selected from the group consisting of
   —O—(C═O)—CH═CH$_2$, —O—(C═O)—C(CH$_3$)═CH$_2$, —(C═O)—CH═CH$_2$, —(C═O)—C(CH$_3$)═CH$_2$, —CH═CH$_2$, —C(CH$_3$)═CH$_2$ and —O—CH═CH$_2$,
   each index e is an integer, which independently of any further indices e is selected from the group of integers 1, 2, 3 and 4,
   each index x independently of any further indices x represents 0 or 1,
   each Y in the structure $Q(Y_xZ_e)_b$ where x=1 represents a structure element, which bonds the polyalicyclic structure element Q with e structure elements Z, wherein each Y is selected independently of any further structure elements Y,
   (a2) one, two or a plurality of radically polymerizable monomers selected from the group consisting of methyl methacrylate, ethyl methacrylate, propyl methacrylate, butyl methacrylate and pentyl methacrylate, wherein component (a2) is present in an amount ranging from 5 to 45 weight percent, base on the total weight of the lacquer composition,
   (a3) optionally one, two or a plurality of further radically polymerizable monomers selected from the group consisting of monomers with three or a plurality of (meth)acrylate groups, wherein the further radically polymerizable monomers of component (a3) are not monomers according to the definitions under (a1) or (a2),
   and
   (a4) optionally one, two or a plurality of further radically polymerizable monomers from the group consisting of acrylates and methacrylates, preferably from the group of methacrylates, wherein the further radically polymerizable monomers of component (a4) are not monomers according to the definitions under to (a1), (a2) or (a3),
   and
   (b) one or a plurality of initiators and/or catalysts
   and
   (c) optionally a filler component comprising one, two or a plurality of fillers,
   (d) optional y one or a plurality of other additives.

2. The lacquer composition according to claim 1 Wherein said radically polymerizable monomers of (a3) comprise three to six (meth)acrylate groups.

3. The lacquer composition according to claim 1, wherein the structure element Q of the compounds of structure $Q(Y_xZ_e)_b$ of component (a1) represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical.

4. The lacquer composition according to claim 1, wherein one, two or a plurality of compounds of structure $Q(Y_xZ_e)_b$, have a tricyclo[5.2.1.0$^{2,6}$]-decane or tricyclo[5.2.1.0$^{2,6}$]-decene structure element and Z is selected from the group consisting of —O—(C═O)—CH═CH$_2$ and —O—(C═O)—C(CH$_3$)═CH$_2$.

5. The lacquer composition according to claim 1, wherein the total quantity of component (a1) and component (a2) is at least 25 wt. %, in relation to the total weight of the lacquer composition.

6. The lacquer composition according to claim 1, wherein the ratio of the weight of component (a1) to the total weight of components (a2), (a3), and (a4) is preferably in the range 4:1 through 1:6.

7. The lacquer composition according to claim 1, wherein the monomer component (a) comprises
   (a1) one, two or a plurality of monomers of structure $Q(Y_xZ_e)_b$ of component (a1), wherein Z represents a —O—(C═O)—CH═CH$_2$, —O—(C═O)—C(CH$_3$)═CH$_2$, —(C═O)—CH═CH$_2$ or —(C═O)—C(CH$_3$)═CH$_2$ group,
   (a2) one, two or a plurality of radically polymerizable monomers from the group consisting of methyl methacrylate, ethyl methacrylate, propyl methacrylate, butyl methacrylate and pentyl methacrylate,
   (a3) one, two or a plurality of further radically polymerizable monomers with three or a plurality of (meth)acrylate groups, wherein the further radically polymerizable monomers of component (a3) are not monomers according to the definitions under (a1)) or (a2),
   and
   (a4) optionally one, two or a plurality of further radically polymerizable monomers from the group consisting of acrylates and methacrylates, wherein the further radically polymerizable monomers of component (a4) are not monomers according to the definitions under (a1), (a2) or (a3).

8. The lacquer composition according to claim 7, wherein said radically polymerizable monomers of (a3) comprise three to six (meth)acrylate groups, and
said radically polymerizable monomers of (a4) comprise methacrylates.

9. The lacquer composition according to claim 1, wherein component (a2) comprises methyl methacrylate or consists of methyl methacrylate.

10. The lacquer composition according to claim 1, wherein component (a1) comprises or consists of bis(methacrylolyoxymethyl)tricyclo[5.2.1.0$^{2,6}$]decane and/or bis(acrylolyoxymethyl)tricyclo[5.2.1.0$^{2,6}$]decane.

11. The lacquer composition according to claim 1, wherein it is photocurable and/or chemically curable.

12. The lacquer composition according to claim wherein component
(b) of the lacquer composition contains one or a plurality of initiators from the group of phosphine oxides,
and/or
c) contains 0 through 60 wt. % of a filler component, comprising one, two or a plurality of fillers.

13. The lacquer composition according to claim 12, wherein component (b) of the lacquer composition comprises an acyl phosphine oxide.

14. The lacquer composition according to claim 1, wherein the lacquer composition is transparent.

15. The lacquer composition according to claim 1, wherein a water absorption of the lacquer composition in the cured state is less than 50 µg/mm$^3$.

16. A method of applying a coating on a surface, comprising:
applying a lacquer composition according to claim 1 to a surface.

17. The method as claimed in claim 16, wherein said surface is a tissue of a patient.

18. The method as claimed in claim 16, wherein said surface is a tooth of a patient.

19. The method as claimed in claim 16, wherein said lacquer composition produces a protective and/or gloss lacquer.

20. A product obtainable by curing a lacquer composition according to claim 1.

21. The product according to claim 20, wherein said product comprises said cured lacquer composition on a surface.

22. A method of performing a dental procedure, comprising: applying a lacquer composition according to claim 1 to tissue of a patient.

23. The method as claimed in claim 22, wherein said lacquer composition functions: as a cavity and/or surface lacquer; as an underfilling of dental fillings materials; to protect the tooth enamel; to prevent cavities; to protect a restoration; to improve the resistance to abrasion of a dental filing material; to stabilize restored surfaces; to protect against abrasion and/or discoloration of a tooth or a restoration; to close marginal gaps and/or microcracks; to smooth restored surfaces; to provide a natural sheen to a tooth or restoration; and to reduce deposition of coloring matter on a tooth or a restoration.

* * * * *

UNITED STATES PATENT AND TRADEMARK OFFICE
CERTIFICATE OF CORRECTION

PATENT NO. : 8,697,769 B2  
APPLICATION NO. : 13/248995  
DATED : April 15, 2014  
INVENTOR(S) : Tobias Blömker et al.

Page 1 of 2

It is certified that error appears in the above-identified patent and that said Letters Patent is hereby corrected as shown below:

IN THE CLAIMS

In Column 57, line 29 of Claim 1 reads "gen atoms or trifluormethyi groups"

but should read "gen atoms or trifluormethyl groups"

In Column 57, line 32 of Claim 1 reads "each Z represent a structure element, Which inde-"

but should read "each Z represent a structure element, which inde-"

In Column 57, line 54 of Claim 1 reads "amount ranging from 5 to 45 weight percent, base on"

but should read "amount ranging from 5 to 45 weight percent, based on"

In Column 58, line 9 of Claim 1 reads "(d) optional y one or a plurality of other additives"

but should read "(d) optionally one or a plurality of other additives"

In Column 58, line 10 of Claim 2 reads "2. The lacquer composition according to claim 1 Wherein"

but should read "2. The lacquer composition according to claim 1, wherein"

Signed and Sealed this  
Thirteenth Day of October, 2015

Michelle K. Lee  
*Director of the United States Patent and Trademark Office*

CERTIFICATE OF CORRECTION (continued)
U.S. Pat. No. 8,697,769 B2

In Column 58, line 48 of Claim 7 reads "ing to the definitions under (a1)) or (a2),"

but should read "ing to the definitions under (a1) or (a2),"

In Column 59, line 3 of Claim 12 reads "12. The lacquer composition according to claim wherein"

but should read "12. The lacquer composition according to claim 1, wherein"

In Column 59, line 16 of Claim 15 reads "15. The lacquer composition according to claim 1, wherein"

but should read "15. The lacquer composition according to claim 1, where"